(12) United States Patent
Okudaira

(10) Patent No.: US 10,792,147 B2
(45) Date of Patent: Oct. 6, 2020

(54) OPHTHALMIC LENS AND METHOD OF MANUFACTURING OPHTHALMIC LENS

(71) Applicant: Nikon Corporation, Minato-ku, Tokyo (JP)

(72) Inventor: Yosuke Okudaira, Konosu (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 16/804,969

(22) Filed: Feb. 28, 2020

(65) Prior Publication Data

US 2020/0197163 A1 Jun. 25, 2020

Related U.S. Application Data

(63) Continuation of application No. PCT/JP2018/029891, filed on Aug. 9, 2018.

(51) Int. Cl.
*A61F 2/16* (2006.01)
*A61F 2/14* (2006.01)
(Continued)

(52) U.S. Cl.
CPC .......... *A61F 2/1618* (2013.01); *A61F 2/1451* (2015.04); *A61F 2/1602* (2013.01);
(Continued)

(58) Field of Classification Search
CPC .... A61F 2/1618; A61F 2/1451; A61F 2/1602; A61F 2/1648; A61F 2/1627;
(Continued)

(56) References Cited

U.S. PATENT DOCUMENTS 5,117,306 A 5/1992 Cohen
2006/0098163 A1* 5/2006 Bandhauer ............ A61F 2/1654
351/159.41
(Continued)

FOREIGN PATENT DOCUMENTS

EP 0 605 841 A1 7/1994
JP 2007-524110 A 8/2007
(Continued)

OTHER PUBLICATIONS

"Handbook of Optical Systems: vol. 4 Survey of Optical Instruments" (WILEY-VCH Verlag GmbH & Co. KGaA, Weinheim), Chapter 36, Section 4, compiled by Herbert Gross in 2008.
(Continued)

*Primary Examiner* — David H Willse
*Assistant Examiner* — Tiffany P Shipmon
(74) *Attorney, Agent, or Firm* — SGPatents PLLC

(57) ABSTRACT

An ophthalmic lens to be attached in or near an eyeball includes a first region that is near an optical axis; a second region that is farther from the optical axis than the first region; and a third region that is farther from the optical axis than the second region, the first region applies a first phase difference of 3 rad or more of a third phase difference with respect to the third region; the second region applies a second phase difference continuously connecting phase differences of the first region and the third region, and continuously changing in accordance with a distance from the optical axis; and the third region applies the third phase difference varying in accordance with the distance from the optical axis around a reference value, wherein a variation amplitude of the third phase difference is not less than 0.1 rad and less than the first phase difference.

20 Claims, 11 Drawing Sheets

(51) Int. Cl.
*G02C 7/02* (2006.01)
*G02C 7/04* (2006.01)

(52) U.S. Cl.
CPC ........ *A61F 2/1648* (2013.01); *A61F 2240/00* (2013.01); *G02C 7/022* (2013.01); *G02C 7/028* (2013.01); *G02C 7/04* (2013.01); *G02C 2202/12* (2013.01)

(58) Field of Classification Search
CPC ..... A61F 2240/00; G02C 7/022; G02C 7/028; G02C 2202/12; G02C 2202/18; B29D 11/00355
See application file for complete search history.

(56) References Cited

U.S. PATENT DOCUMENTS

| | | | |
|---|---|---|---|
| 2009/0088840 A1 | 4/2009 | Simpson et al. | |
| 2009/0268158 A1 | 10/2009 | Weeber | |
| 2010/0161051 A1* | 6/2010 | Hong | G02C 7/041 623/6.27 |
| 2010/0274234 A1 | 10/2010 | Liang | |
| 2011/0029073 A1* | 2/2011 | Liang | A61F 2/1648 623/5.11 |
| 2011/0234974 A1 | 9/2011 | Lawu | |
| 2011/0267693 A1 | 11/2011 | Kobayashi et al. | |
| 2012/0283825 A1 | 11/2012 | Houbrechts et al. | |
| 2012/0323319 A1 | 12/2012 | Cohen et al. | |
| 2014/0009736 A1 | 1/2014 | Zhao | |
| 2014/0347624 A1 | 11/2014 | Ando et al. | |
| 2015/0022775 A1 | 1/2015 | Ando et al. | |
| 2017/0227789 A1 | 8/2017 | Ando et al. | |
| 2017/0273781 A1* | 9/2017 | Zhao | G02C 7/042 |

FOREIGN PATENT DOCUMENTS

| | | |
|---|---|---|
| JP | 2009-082723 A | 4/2009 |
| JP | 2010-134282 A | 6/2010 |
| JP | 2012-512709 A | 6/2012 |
| JP | 2013-517822 A | 5/2013 |
| JP | 2013-168195 A | 8/2013 |
| JP | 2016-150213 A | 8/2016 |
| WO | WO 2004/113994 A2 | 12/2004 |
| WO | WO 2010/079528 A1 | 7/2010 |
| WO | WO 2013/118176 A1 | 8/2013 |
| WO | WO 2013/118177 A1 | 8/2013 |
| WO | WO 2013/122175 A1 | 8/2013 |
| WO | WO 2016/021075 A1 | 2/2016 |
| WO | WO 2019/020435 A1 | 1/2019 |

OTHER PUBLICATIONS

International Search Report from International Patent Application No. PCT/JP2018/029891, dated Nov. 6, 2018.

\* cited by examiner

PUPIL DIAMETER
3mm

PUPIL DIAMETER
4mm

PUPIL DIAMETER
6mm

PUPIL DIAMETER 3mm

PUPIL DIAMETER 4mm

PUPIL DIAMETER 6mm

PUPIL DIAMETER
3mm

PUPIL DIAMETER
4mm

PUPIL DIAMETER
6mm

PUPIL DIAMETER
3mm

PUPIL DIAMETER
4mm

PUPIL DIAMETER
6mm

OPHTHALMIC LENS AND METHOD OF MANUFACTURING OPHTHALMIC LENS

TECHNICAL FIELD

The present invention relates to an ophthalmic lens such as an intraocular lens and a method of manufacturing the ophthalmic lens.

BACKGROUND ART

There have been used an intraocular lens (IOL) to be load into an eyeball instead of a crystalline lens after extraction of the crystalline lens, a phakic intraocular lens (PIL) to be loaded into an eyeball in combination with the crystalline lens, and an ophthalmic lens that is used in contact with the eyeball, such as contact lens. Further, multifocal type ophthalmic lenses have been used to supplement the focusing power of the eye. As one of the multifocal ophthalmic type lenses, a multifocal type ophthalmic lens having a central refractive region providing one refractive focusing ability and a diffractive region providing near diffraction focusing ability and far diffraction focusing ability has been proposed (see PTL1).

CITATION LIST

Patent Literature

PTL1: Japanese Laid-Open Patent Publication No. 2009-82723, which is the counterpart of US Laid-Open Patent Publication No. US2009/088840A1.

SUMMARY OF INVENTION

An ophthalmic lens to be attached in or near an eyeball according to the 1st aspect comprises: a first region that is near an optical axis; a second region that is farther from the optical axis than the first region; and a third region that is farther from the optical axis than the second region, wherein: in a state where the ophthalmic lens is attached to the eyeball, light rays passing through the first region, the second region, and the third region form an image on a retina; the first region applies a first phase difference of 3 rad or more of a third phase difference to the light ray passing through the first region with respect to the light ray passing through the third region; the second region applies a second phase difference to the light ray passing through the second region, the second phase difference continuously connecting phase differences of the light ray passing through the first region and the light ray passing through the third region, and continuously changing in accordance with a distance from the optical axis; and the third region applies the third phase difference to the light ray passing through the third region, the third phase difference varying in accordance with the distance from the optical axis around a reference value, wherein a variation amplitude of the third phase difference is not less than 0.1 rad and less than the first phase difference.

DESCRIPTION OF EMBODIMENTS

One Embodiment

Figure 1A:
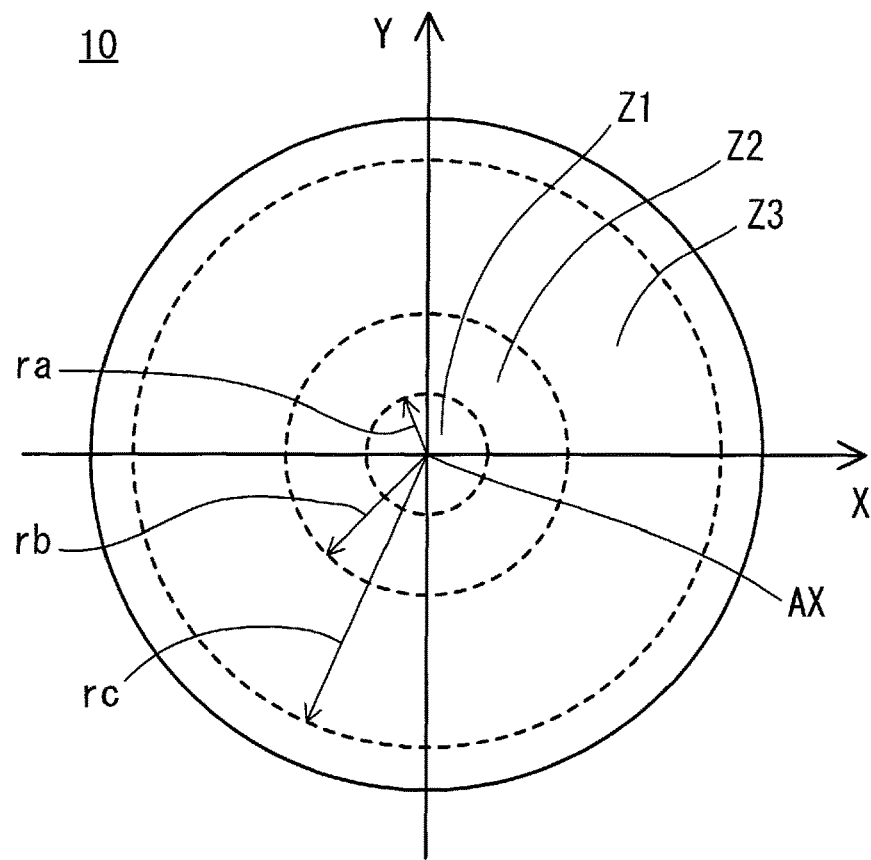
FIG. 1A is a top view showing an ophthalmic lens according to an embodiment of the present invention.
Figure 1B:
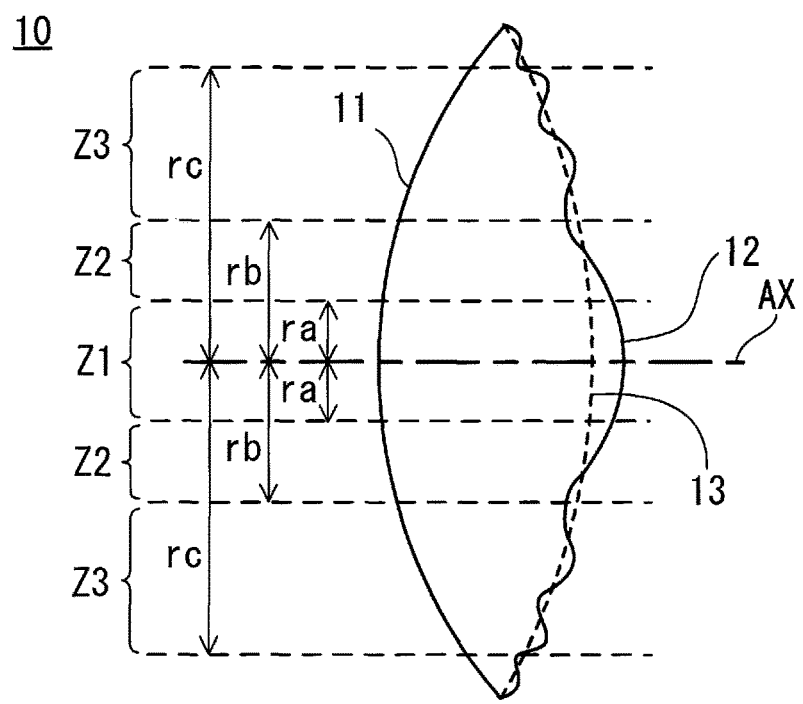
FIG. 1B is a cross-sectional view showing the ophthalmic lens shown in FIG. 1A.

FIG. 1A and FIG. 1B are views showing an intraocular lens 10 as an example of an ophthalmic lens according to one embodiment of the present invention. FIG. 1A shows a top view and FIG. 1B shows a cross-sectional view taken through the Y-axis in FIG. 1A. The intraocular lens 10 has two refractive surfaces, that is, a light incident surface 11 and a light exit surface 12. As one example, the incident surface 11 is a spherical surface, and the exit surface 12 is a surface (a phase difference forming surface) having smooth unevenness with respect to a reference surface 13 which is a spherical surface. An optical axis AX of the intraocular lens 10 is a rotationally symmetric axis of the incident surface 11 and the exit surface 12 (or the reference surface 13). The X-axis and the Y-axis shown in FIG. 1A are axes that are in any directions in a plane perpendicular to the optical axis AX and that are orthogonal to each other. The intraocular lens 10 may have a support unit (not shown) therearound.

A degree of smooth unevenness of the exit surface 12 with respect to the reference surface 13 is determined in accordance with a distance from the optical axis AX in a direction away from the optical axis AX, as described later. The above-mentioned uneven shape is therefore a rotationally symmetric shape with respect to the optical axis AX. Note that the uneven shape of the exit surface 12 is exaggerated in the optical axis AX direction in FIG. 1B. A portion having the above-mentioned uneven shape may be interpreted as a higher-order shape portion that changes with a higher-order function for the distance from the optical axis AX. For example, a first region, a second region, and a third region of the intraocular lens 10 are higher-order shape portions that change with a high-order function based on the distance from the optical axis AX.

In the present embodiment, a region of the intraocular lens 10 near the optical axis AX on the exit surface 12 (or the incident surface 11), for example, a region within a radius ra from the optical axis AX is referred to as a first region Z1, as shown in FIG. 1A. Further, a region farther from the optical axis AX than the first region Z1, for example, a region that is equal to or more than the radius ra and equal to or less than a radius rb from the optical axis AX is referred to as a second region Z2. Furthermore, a region farther from the optical axis AX than the second region Z2, for example, a region that is equal to or more than the radius rb and equal to or less than a radius rc from the optical axis AX is referred to as a third region Z3.

Note that the shapes of the incident surface 11 and the reference surface 13 may be so-called aspherical surfaces, such as elliptical surfaces, oblate spherical surfaces, or parabolic surfaces, instead of spherical surfaces. Further, the shapes may be either concave or convex surfaces, or a planar surface.

Furthermore, the above-mentioned uneven shape may be formed not on the exit surface 12, but on the incident surface 11. Alternatively, the shape may be formed both on the incident surface 11 and on the exit surface 12.

The intraocular lens 10 is made of, for example, an acrylic resin material (for example, a copolymer of acrylate and methacrylate), hydrogel, or silicone. Further, the ophthalmic lens (for example, the intraocular lens 10) includes a soft lens made of a foldable flexible material (for example, an acrylic resin material or silicone).

Figure 2:
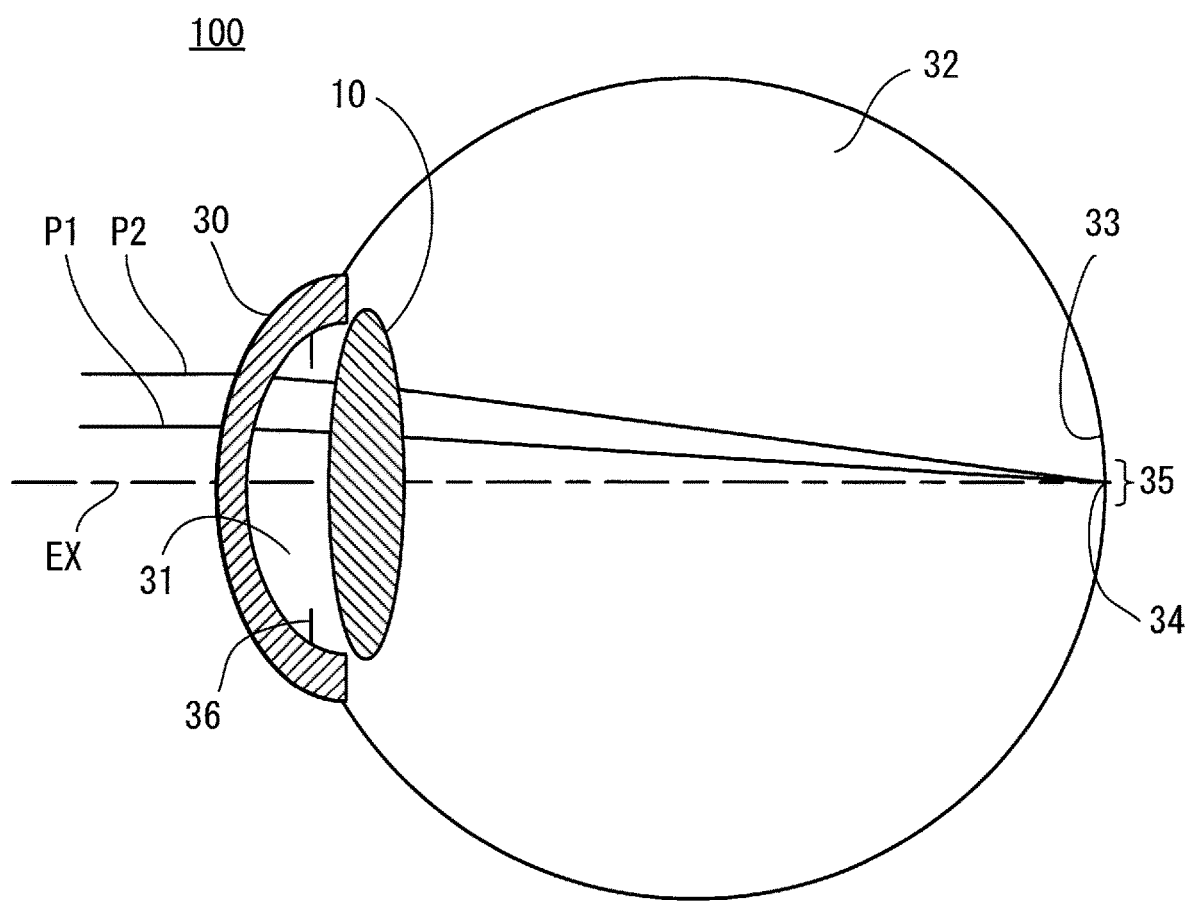
FIG. 2 is a view showing a cross-section of an eyeball to which the ophthalmic lens according to the embodiment is attached.

FIG. 2 is a view showing a cross-section of an eyeball 100 loaded with the intraocular lens 10 according to the one embodiment of the present invention. The intraocular lens 10 shown in FIG. 2 is a lens (in this case, an IOL) loaded in the eyeball 100 in place of a crystalline lens (not shown) extracted from the eyeball, and arranged at a position between a vitreous body 32 and an anterior chamber 31, where the crystalline lens would otherwise be located. An iris 36 is located inside the anterior chamber 31. The intraocular lens 10 is arranged so that its optical axis AX substantially, but not necessarily precisely, coincides with a center line EX of the eyeball, which is a straight line formed by connecting the center of a cornea 30 and the center of a macula 35.

The intraocular lens 10 is a lens having a refractive power similar to that of the original crystalline lens. Light rays P1, P2 from an external object (not shown) are refracted at the cornea 30 and go through the anterior chamber 31, the intraocular lens 10, and the vitreous body 32 to form an image at an imaging point 34 near the center of the macula 35 on the retina 33.

The two light rays P1, P2 shown in FIG. 2 are illustrated only for the purpose of example. Actually, a large number of light rays (for example, imaging light rays) originating from an object and entering the incident surface go through the cornea 30, the intraocular lens 10, and the like described above to form an image at the imaging point 34 on the retina 33. So long as an optical system including the cornea 30, the anterior chamber 31, the intraocular lens 10, and the vitreous body 32 has no aberration, a large number of imaging light rays have no optical path length difference one another.

In the present embodiment, as shown in FIG. 1B, the phase difference forming surface having an uneven shape or the like is formed in the exit surface 12 of the intraocular lens 10, so that phase differences (for example, an optical path length differences) caused by the shape (for example, the uneven shape) of the exit surface 12 are applied to a large number of imaging light rays from the object when they transmit through the intraocular lens 10.

Figure 3A:
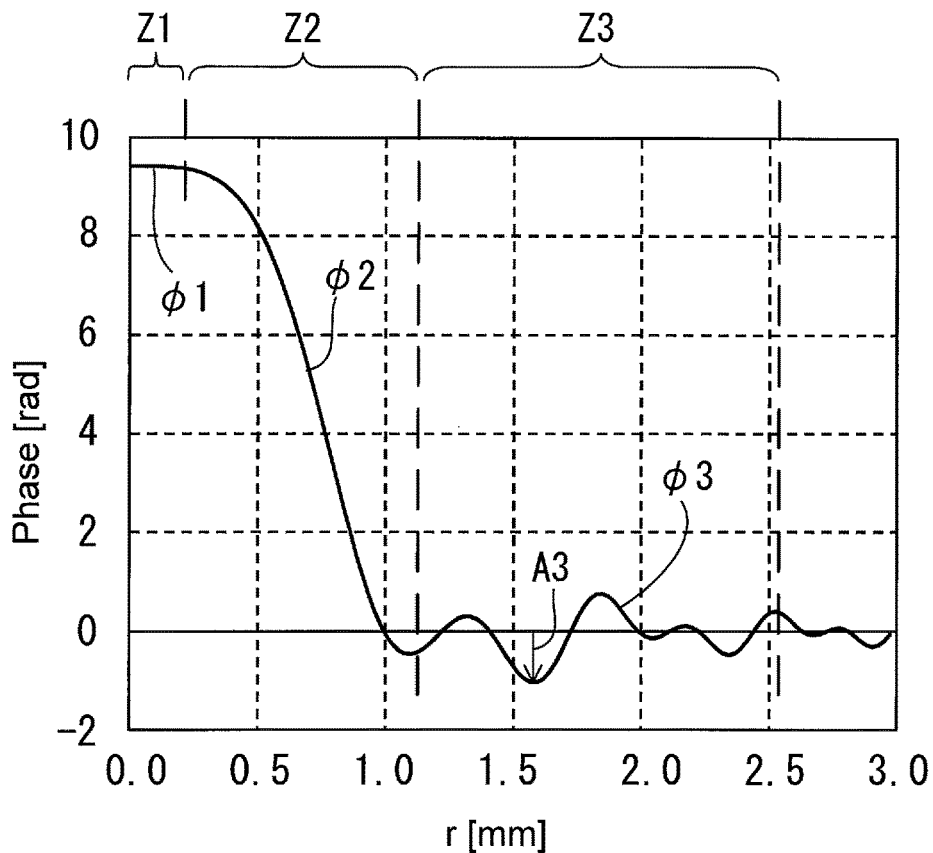
FIG. 3A is a view showing a phase change applied to an imaging light ray in an eyeball to which an ophthalmic lens according to the embodiment is attached.

FIG. 3A is a graph showing a phase difference (for example, an optical path length difference) of each of the imaging light rays reaching the imaging point 34 from an object, in the eyeball 100 loaded with the intraocular lens 10 according to the present embodiment (in the optical system consisting of the cornea 30, the anterior chamber 31, the intraocular lens 10, and the vitreous body 32).

The horizontal axis of the graph in FIG. 3A represents a position through which the imaging light ray passes, as a distance r from the optical axis AX of the intraocular lens 10, and the vertical axis of the graph of FIG. 3A represents an optical path length difference as a phase difference (Phase, radian) of a center wavelength (for example, 550 nm as a design wavelength) of light used in the intraocular lens. When the position through which the imaging light ray passes is (x, y) of the XY coordinates shown in FIG. 1A, $r=\sqrt{(x^2+y^2)}$.

As shown in FIG. 3A, with the intraocular lens 10 of the present embodiment, each imaging light ray reaching the imaging point 34 from the object is given a phase difference (for example, an optical path length difference) in accordance with a distance r from the optical axis AX at which the imaging light ray passes through the intraocular lens 10.

For example, a light ray passing through the third region Z3 which is far from the optical axis AX is given a third phase difference $\varphi 3$ that varies in accordance with the distance from the optical axis AX around 0 [rad], which is a reference value as an average value of the third phase difference $\varphi 3$ in the third region Z3. The third phase difference $\varphi 3$ varies substantially periodically in accordance with the distance from the optical axis AX. The maximum value of the absolute value of a difference between the third phase difference $\varphi 3$ in the third region Z3 and 0 [rad], which is the reference value, is referred to as a variation amplitude A3.

On the other hand, a light ray passing through the first region Z1 near the optical axis AX is given a first phase difference $\varphi 1$ of approximately 9.5 [rad] with respect to the light ray passing through the third region Z3. Further, a light ray passing through the second region Z2 is given a second phase difference $\varphi 2$ that continuously connects the phase differences of the light ray passing through the first region Z1 and the light ray passing through the third region Z3, and continuously changes in accordance with the distance from the optical axis AX. In other words, the light ray passing through the second region Z2 is given the second phase $\varphi 2$ that continuously connects the first phase difference $\varphi 1$ and the third phase difference $\varphi 3$, and continuously changes based on the distance from the optical axis AX. That is, the phase of each light ray passing through the first region Z1, the second region Z2, or the third region Z3 always continuously changes in accordance with the distance from the optical axis AX, and no discontinuous phase change occurs.

As described above, the exit surface 12 is a surface (a phase difference forming surface) that continuously connects the phase differences applied to the light rays in the first region Z1, the second region Z2, and the third region Z3, and applies the phase differences (the first phase difference $\varphi 1$, the second phase difference $\varphi 2$, and the third phase difference $\varphi 3$) that continuously and smoothly change based on the distance from the optical axis AX. Further, the exit surface 12 is, for example, a surface (phase difference forming surface) that applies a third phase difference $\varphi 3$ in the third region Z3, in addition to applying the first phase difference $\varphi 1$ and the second phase difference $\varphi 2$ to the light ray, where the third phase difference $\varphi 3$ continuously and smoothly varies so as to have the maximum value and the minimum value based on the distance from the optical axis AX. Further, for example, a light ray transmitting through the second region Z2 described above is given the second phase difference $\varphi 2$ that connects (links) the phase differences of the light ray passing through the first region Z1 and the light ray passing through the third region Z3 in a continuous and smooth manner like a curved line, and continuously changes based on the distance from the optical axis AX. Hereinafter, the first phase difference $\varphi 1$, the second phase difference $\varphi 2$, and the third phase difference $\varphi 3$ are collectively referred to as phase differences $\varphi$.

In the present embodiment, by applying the above-mentioned phase differences $\varphi$ to the imaging light rays, a depth of focus of the optical system including the cornea 30, the anterior chamber 31, the intraocular lens 10, and the vitreous body 32 can be increased.

Figure 3B:
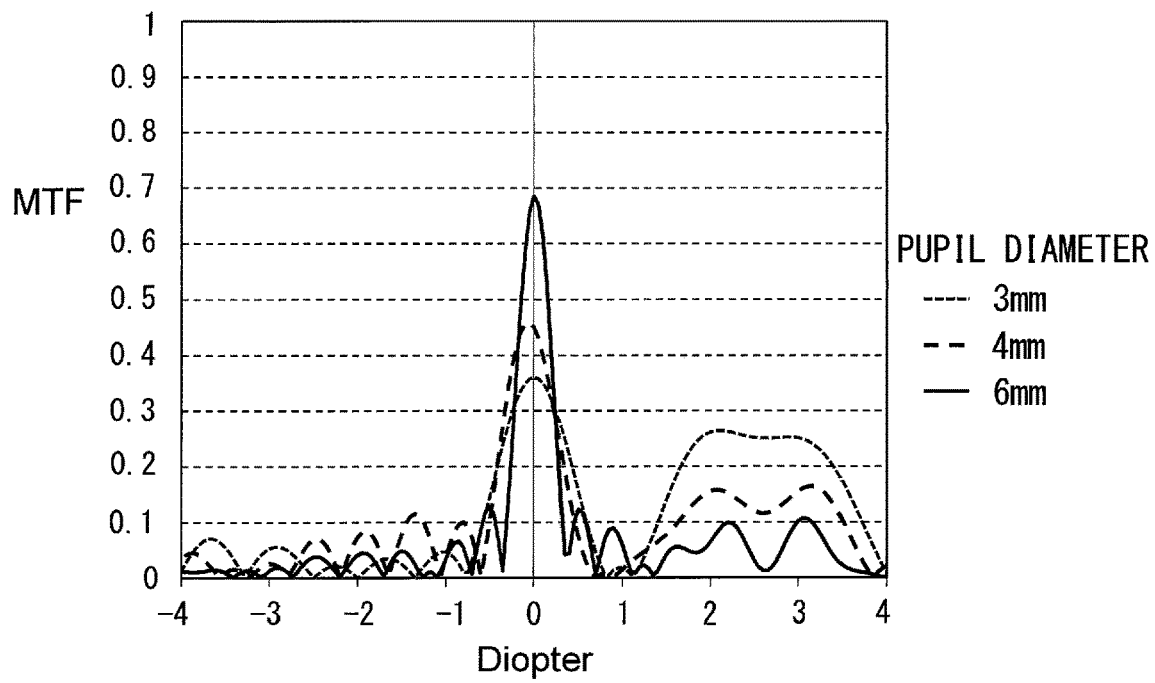
FIG. 3B is a view showing an MTF of an image formed on a retina in an eyeball to which the ophthalmic lens according to the embodiment is attached.

FIG. 3B is a graph showing a simulation result in each diopter of a modulation transfer function (MTF) at a predetermined spatial frequency (for example, approximately 50 [LP/mm]) of an image formed on the retina 33 near the imaging point 34, in the eyeball 100 loaded with the intraocular lens 10 of the present embodiment (in the optical system including the cornea 30, the anterior chamber 31, the intraocular lens 10, and the vitreous body 32).

Figure 4A:
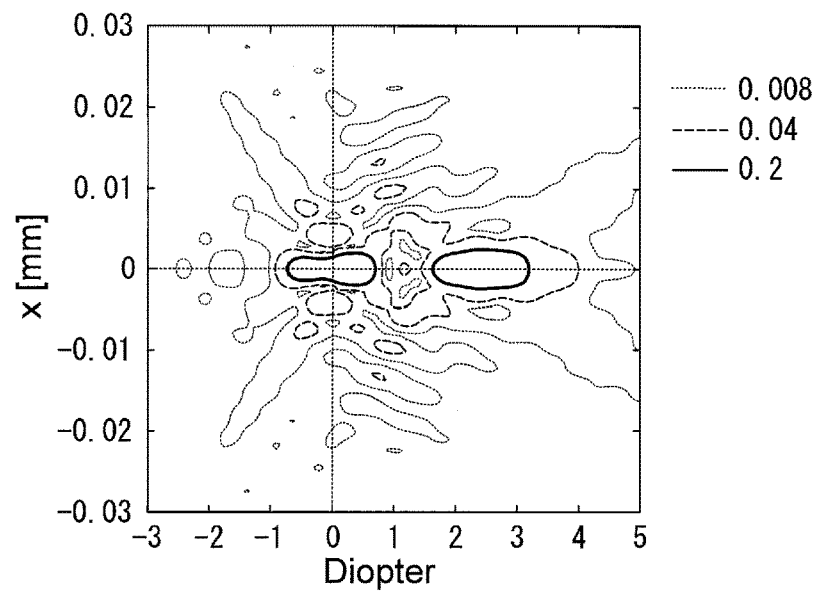
FIG. 4A is a view showing a simulation result of a point spread function formed at a predetermined position (for example, near the retina) in an eyeball to which the ophthalmic lens according to the embodiment is attached in a case where the pupil diameter is 3 mm.
Figure 4B:
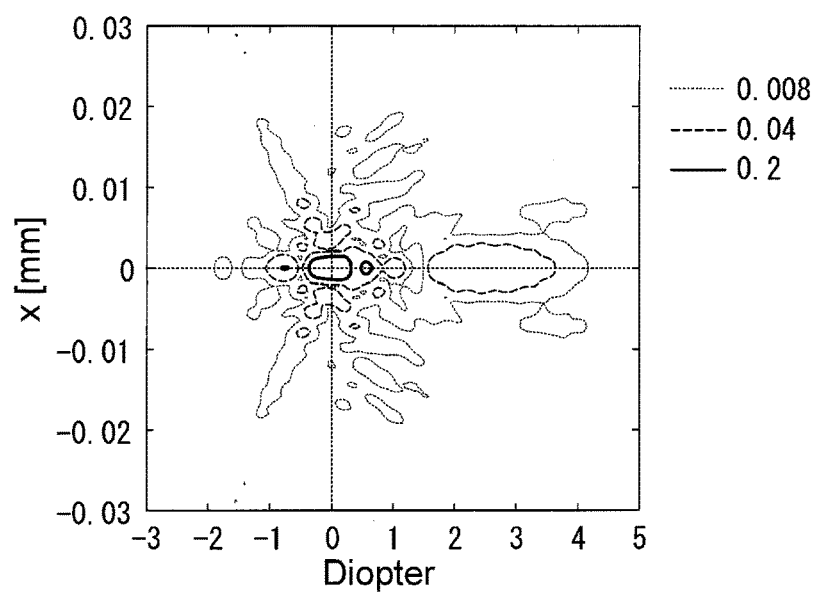
FIG. 4B is a view showing a simulation result of a point spread function formed at a predetermined position (for example, near the retina) in an eyeball to which the ophthalmic lens according to the embodiment is attached in a case where the pupil diameter is 4 mm.
Figure 4C:
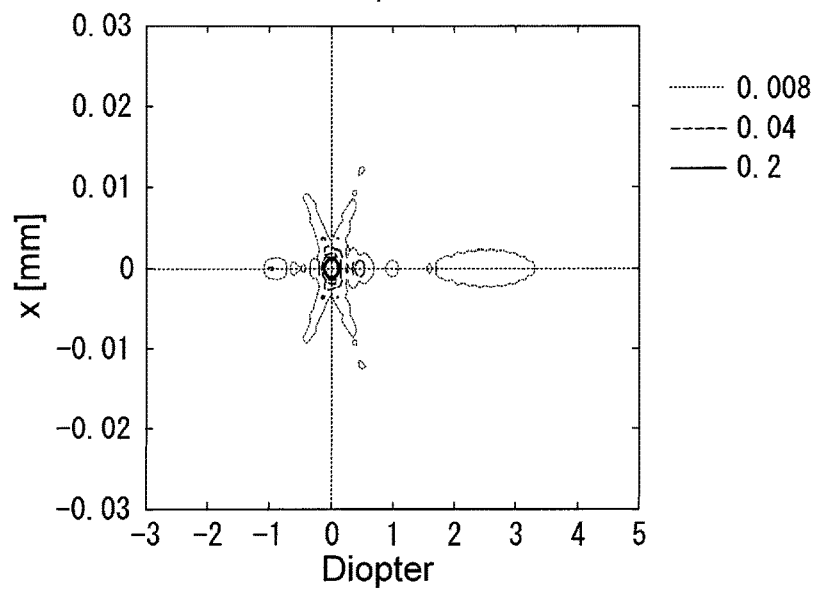
FIG. 4C is a view showing a simulation result of a point spread function formed at a predetermined position (for example, near the retina) in an eyeball to which the ophthalmic lens according to the embodiment is attached in a case where the pupil diameter is 6 mm.

FIG. 4A, FIG. 4B and FIG. 4C are graphs showing simulation results in each diopter of a point spread function (PSF) near the imaging point 34 in the eyeball 100 loaded with the intraocular lens 10 of the present embodiment.

The simulation is based on the Navarro model which is disclosed in "Handbook of Optical Systems: Vol. 4 Survey of Optical Instruments" (WILEY-VCH Verlag GmbH & Co. KGaA, Weinheim), Chapter 36, Section 4, compiled by Herbert Gross in 2008.

That is, assuming the optical system (the optical system including the cornea 30, the anterior chamber 31, the intraocular lens 10, and the vitreous body 32) has a focal length according to the above-mentioned Navarro model, the simulation was performed by applying a phase difference (for example, an optical path length difference) shown in FIG. 3A to each imaging light ray passing through the optical system.

FIG. 3B is a graph showing a simulation result of the MTF as described above, and shows three types of MTFs in cases where a pupil diameter (a diameter of an opening of the iris 36) is 3 mm, 4 mm, and 6 mm. The vertical axis of the graph represents a modulation transmitting rate of a spatial frequency component (for example, approximately 50 [LP/mm]) of an image on the retina 33, and the horizontal axis represents a defocus amount in the center line EX direction (a defocus amount when an object is moved in the center line EX direction) in diopters. For example, when an image of an object located at infinity is formed at a position of 0 diopters on the horizontal axis, an image of an object located one meter away from the eyeball 100 is formed at a position of +1 diopter on the horizontal axis. Note that when the intraocular lens is ideally attached to the eyeball by an ophthalmic surgery or the like, the center line EX and the optical axis AX coincide each other.

FIG. 4A is a graph (a contour map) showing a point spread function in a case where the pupil diameter (the diameter of the opening of the iris 36) is 3 mm. The vertical axis of the graph represents a distance from a center line EX of an eyeball on the retina 33, and the horizontal axis represents a defocus amount in the center line EX direction in diopters, as in FIG. 3B. Three contour lines constituting a point spread function represent contour lines on which intensities are 0.2, 0.04, and 0.008, respectively. The above-described vertical axis, horizontal axis, and contour lines in the point spread function are also used in each of the following figures in the same manner.

FIG. 4B shows a point spread function in a case where the pupil diameter is 4 mm, and FIG. 4C shows a point spread function in a case where the pupil diameter is 6 mm.

Figure 7A:
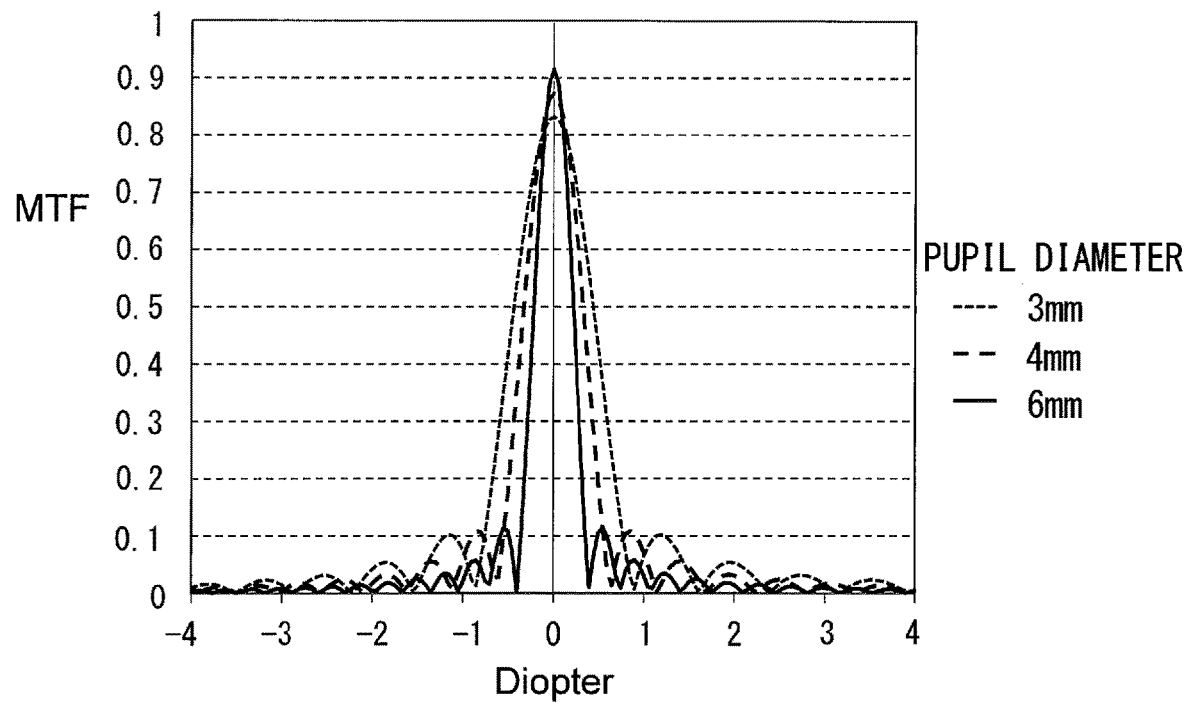
FIG. 7A is a view showing an MTF of an image formed on a retina in an eyeball to which a conventional single-focus ophthalmic lens is attached.

Additionally, FIG. 7A is a graph showing an MTF in a case where a conventional single-focus type intraocular lens is attached to an eyeball, as a comparative example. The pupil diameter and the spatial frequency of the image on the retina 33 used for the simulation are the same as in the case of FIG. 3B.

Figure 8A:
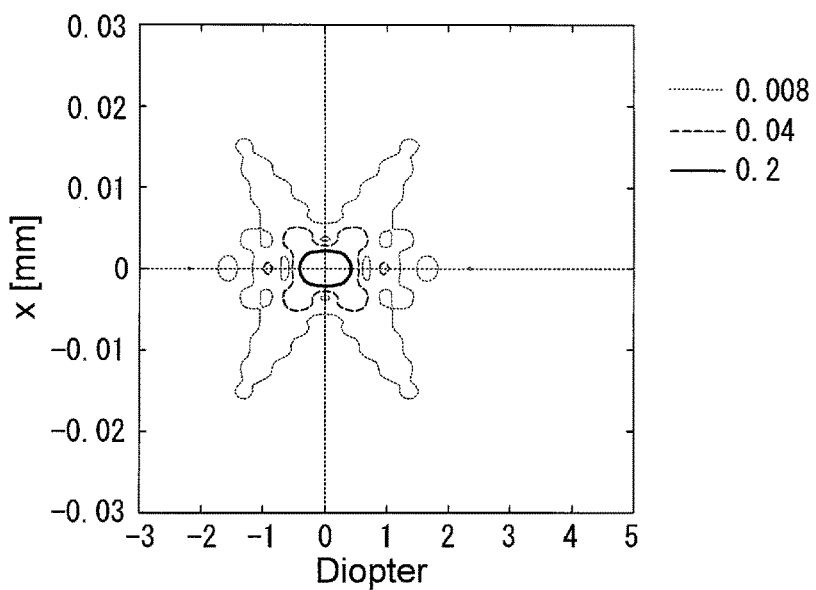
FIG. 8A is a view showing a simulation result of a point spread function formed at a predetermined position (for example, near the retina) in an eyeball to which a conventional single-focus ophthalmic lens is attached in a case where the pupil diameter is 3 mm.
Figure 8B:
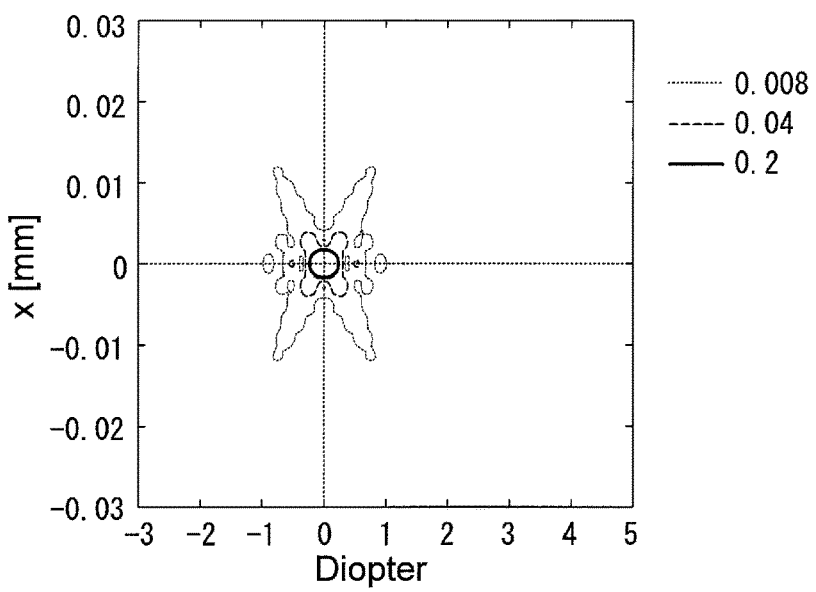
FIG. 8B is a view showing a simulation result of a point spread function formed at a predetermined position (for example, near the retina) in an eyeball to which a conventional single-focus ophthalmic lens is attached in a case where the pupil diameter is 4 mm.
Figure 8C:
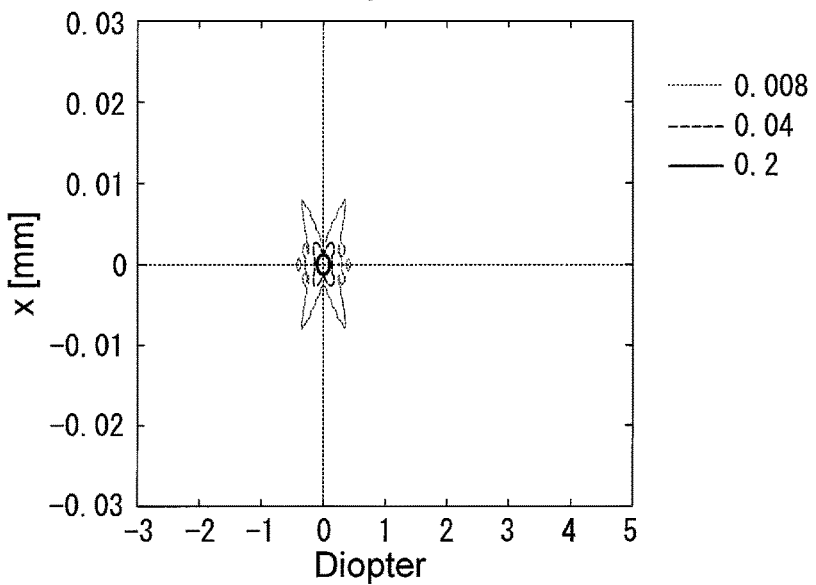
FIG. 8C is a view showing a simulation result of a point spread function formed at a predetermined position (for example, near the retina) in an eyeball to which a conventional single-focus ophthalmic lens is attached in a case where the pupil diameter is 6 mm.

Further, FIG. 8A, FIG. 8B and FIG. 8C are graphs illustrating simulation results of a point spread function in a case where a conventional single-focus type intraocular lens is attached, as a comparative example. FIG. 8A shows a point spread function in a case where the pupil diameter is 3 mm, FIG. 8B shows a point spread function in a case where the pupil diameter is 4 mm, and FIG. 8C shows a point spread function in a case where the pupil diameter is 6 mm.

In comparison of FIG. 3B with FIG. 7A, and FIG. 4A to FIG. 4C with FIG. 8A to FIG. 8C, the intraocular lens 10 of the present embodiment can increase values of the MTF and the point spread function in a defocus position from +2 to +3.5 diopters in each pupil diameter, as compared to the conventional single-focus type intraocular lens. That is, it can be seen that the depth of focus of the eyeball 100 is increased by the intraocular lens 10 of the present embodiment attached to the eyeball 100.

This means that the MTF and point spread function of the intraocular lens 10 of the present embodiment allow to form the best image for an object located at infinity (0 diopters) and form a certain good image for an object located at a distance between 50 cm to 28 cm from the eyeball, which correspond to +2 to +3.5 diopters.

Figure 7B:
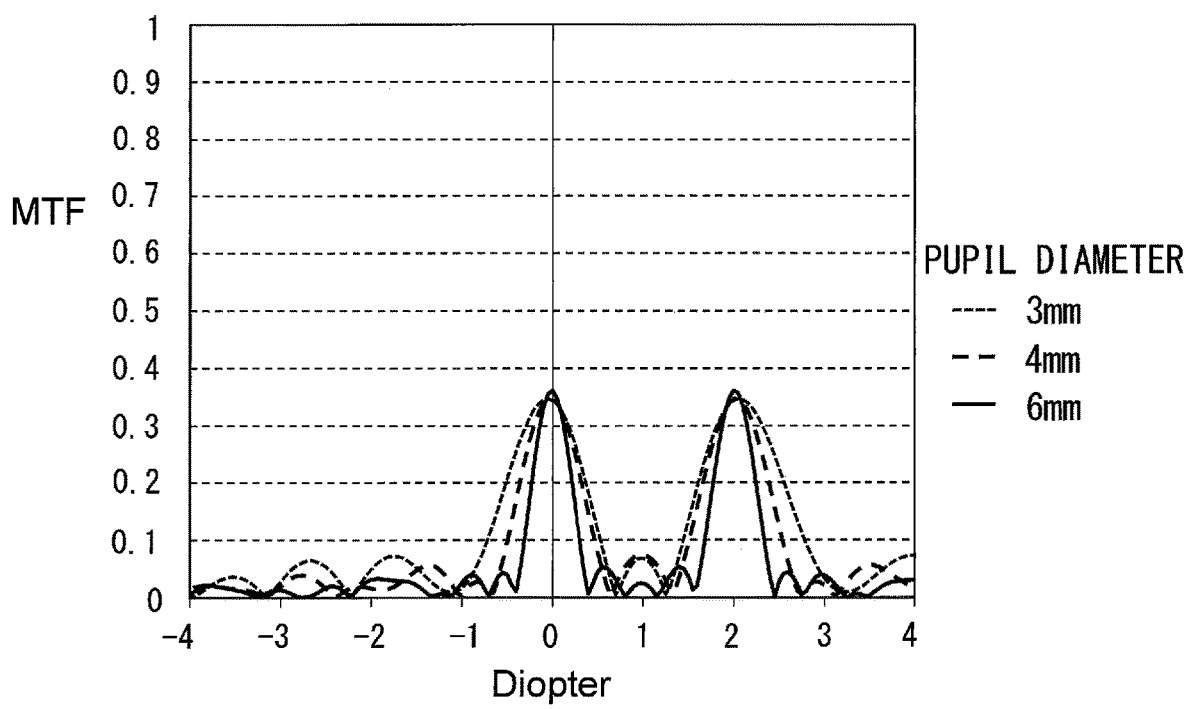
FIG. 7B is a view showing an MTF of an image formed on a retina in an eyeball to which a conventional bifocal ophthalmic lens is attached.
Figure 9A:
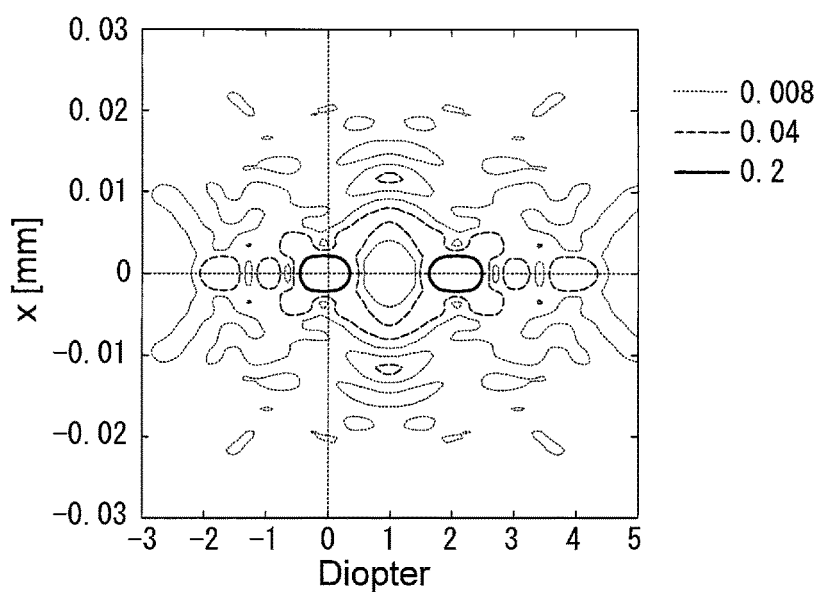
FIG. 9A is a view showing a simulation result of a point spread function formed at a predetermined position (for example, near the retina) in an eyeball to which a conventional bifocal ophthalmic lens is attached in a case where the pupil diameter is 3 mm.
Figure 9B:
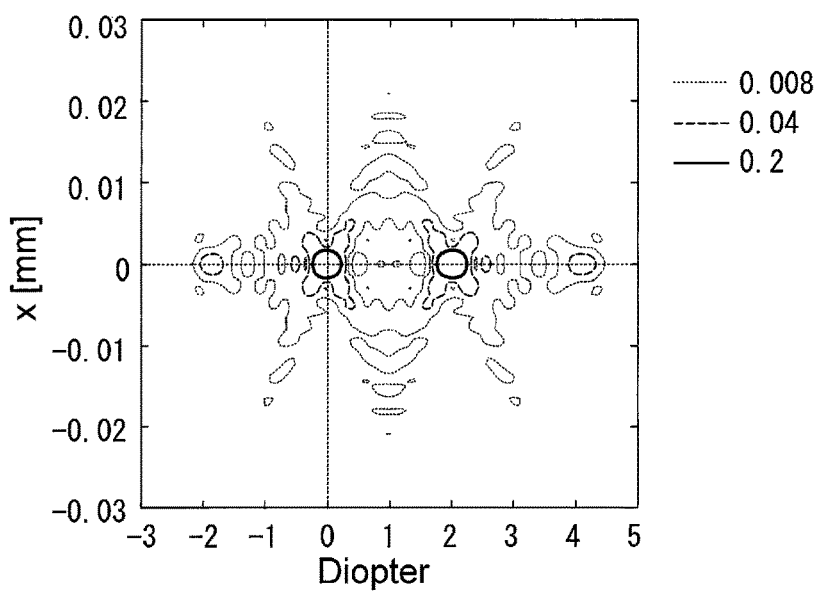
FIG. 9B is a view showing a simulation result of a point spread function formed at a predetermined position (for example, near the retina) in an eyeball to which a conventional bifocal ophthalmic lens is attached in a case where the pupil diameter is 4 mm.
Figure 9C:
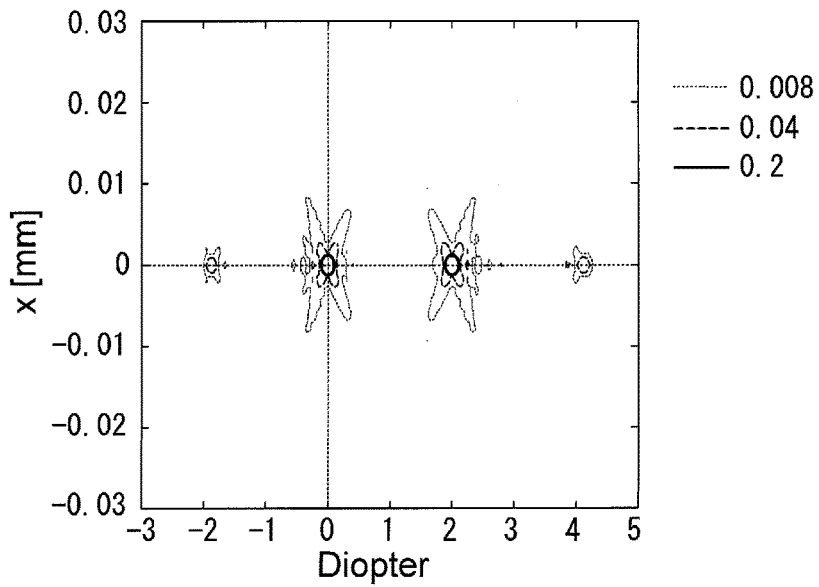
FIG. 9C is a view showing a simulation result of a point spread function formed at a predetermined position (for example, near the retina) in an eyeball to which a conventional bifocal ophthalmic lens is attached in a case where the pupil diameter is 6 mm.

FIG. 7B is a graph showing an MTF in a case where a conventional bifocal type intraocular lens is attached, as a comparative example. The pupil diameter and the spatial frequency of the image on the retina 33 used for the simulation are the same as those shown in FIG. 3B. Further, FIG. 9A, FIG. 9B and FIG. 9C are graphs illustrating simulation results of a point spread function in a case where a conventional bifocal type intraocular lens is attached. FIG. 9A shows a point spread function in a case where the pupil diameter is 3 mm, FIG. 9B shows a point spread function in a case where the pupil diameter is 4 mm, and FIG. 9C shows a point spread function in a case where the pupil diameter is 6 mm. This bifocal type intraocular lens is a lens having two focus positions with a diopter difference of 2.

In comparison of FIG. 3B with FIG. 7B, and FIG. 4A to FIG. 4C with FIG. 9A to FIG. 9C, it can be seen that the MTF and the point spread function increase only near two focus positions (0 diopters and +2 diopters in the conventional figure) in the conventional bifocal type intraocular lens. On the other hand, in the intraocular lens 10 of the present embodiment, the MTF and the point spread function increase, that is, the depth of focus is increased near 0 diopters and in a continuous defocus range from +2 diopters to +3.5 diopters.

In the above-described embodiment, variation of the third phase difference φ3 in the third region Z3 in accordance with the radius r from the optical axis AX serves as a so-called bifocal lens. Then, a period of the variation in the radius r direction is preferably approximately 0.1 to 1.0 mm so that functions as a multifocal lens (for example, a bifocal lens) are efficiently achieved. Additionally, the variation amplitude A3 is preferably not less than 0.1 [rad] and approximately 70% or less of the first phase difference φ1 described above.

First Modification

Figure 5A:
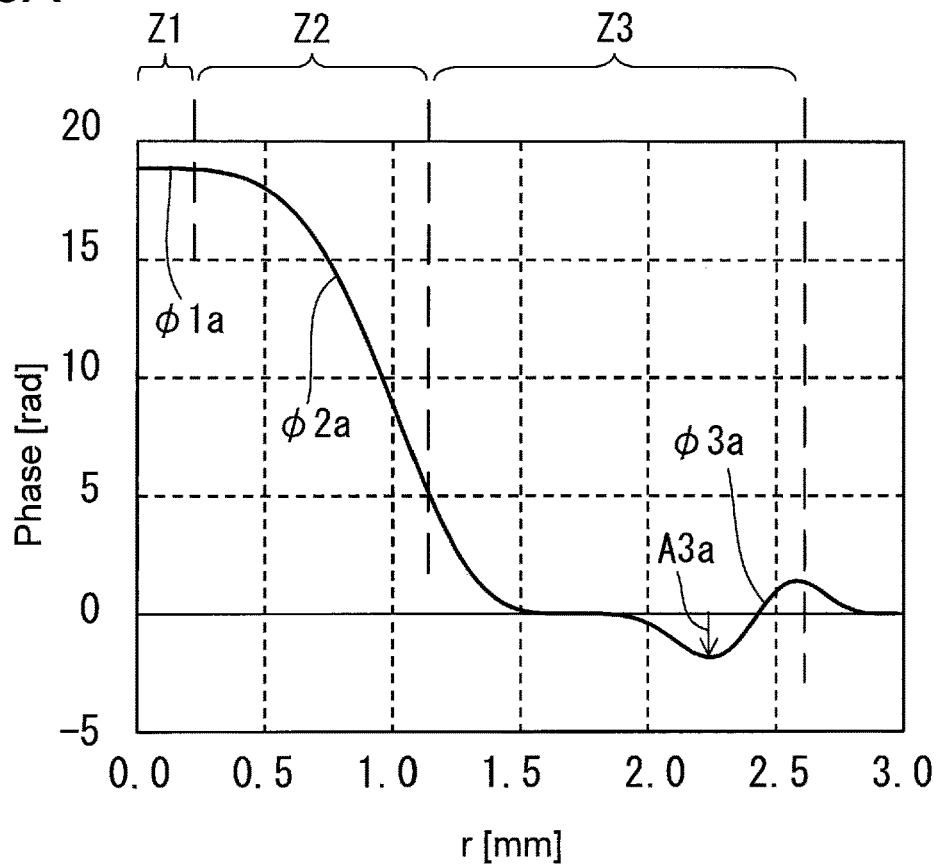
FIG. 5A is a view showing a phase change applied to an imaging light ray in an eyeball to which an ophthalmic lens according to a first modification is attached.

FIG. 5A is a graph showing a phase difference (for example, an optical path length difference) of each imaging light ray reaching the imaging point 34 from an object, in the eyeball 100 loaded with the intraocular lens 10 according to a first modification.

The horizontal axis and the vertical axis in the graph in FIG. 5A are the same as the horizontal axis and the vertical axis in the graph of FIG. 3A.

In the intraocular lens 10 of the first modification, a light ray passing through the third region Z3 which is far from the optical axis AX is given a third phase difference φ3a that varies in accordance with the distance r from the optical axis AX around 0 [rad], which is a reference value as an average value of the third phase difference φ3 in the third region Z3. The maximum value of the absolute value of a difference between the third phase difference φ3a in the third region Z3 and 0 [rad], which is the reference value, is referred to as a variation amplitude A3a.

On the other hand, a light ray passing through the first region Z1 near the optical axis AX is given a first phase difference φ1a of around 18 [rad] with respect to the light ray passing through the third region Z3. Furthermore, a light ray passing through the second region Z2 is given a second phase difference φ2a that continuously connects the phase differences of the light ray passing through the first region Z1 and the light ray passing through the third region Z3, and continuously changes in accordance with the distance r from the optical axis AX.

Figure 5B:
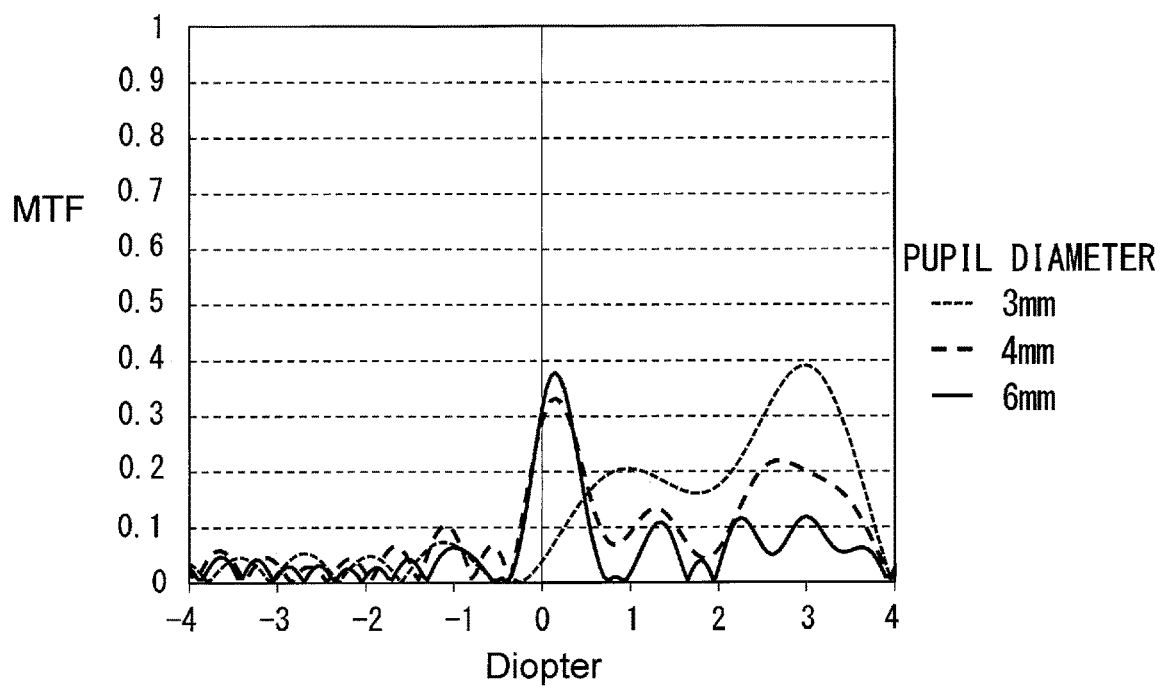
FIG. 5B is a view showing an MTF of an image formed on a retina in an eyeball to which the ophthalmic lens according to the first modification is attached.

FIG. 5B is a graph showing a simulation result in each diopter of a MTF of an image formed on the retina 33 near the imaging point 34, in the eyeball 100 loaded with the intraocular lens 10 of the first modification (in the optical system including the cornea 30, the anterior chamber 31, the intraocular lens 10, and the vitreous body 32). The pupil diameter and the spatial frequency of the image on the retina 33 used for the simulation are the same as in the case of FIG. 3B.

Figure 6A:
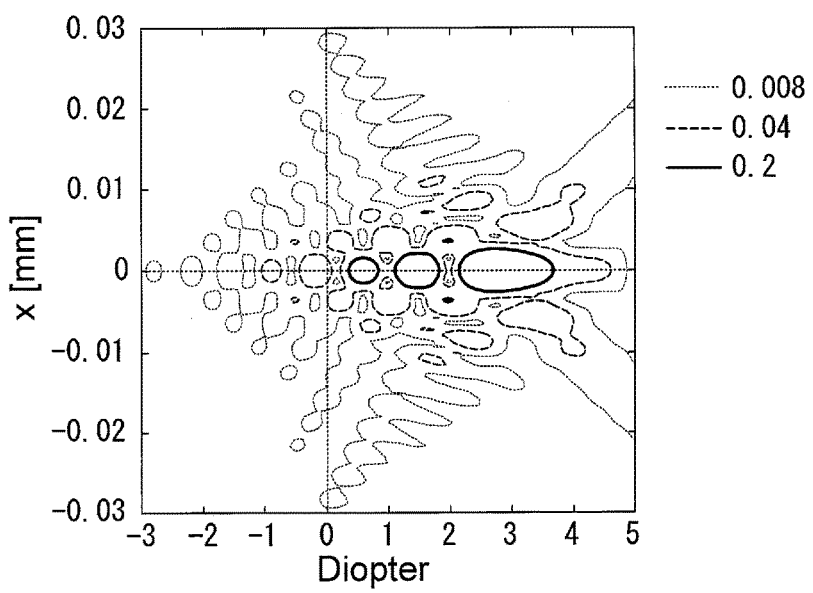
FIG. 6A is a view showing a simulation result of a point spread function formed at a predetermined position (for example, near the retina) in an eyeball to which the ophthalmic lens according to the first modification is attached in a case where the pupil diameter is 3 mm.
Figure 6B:
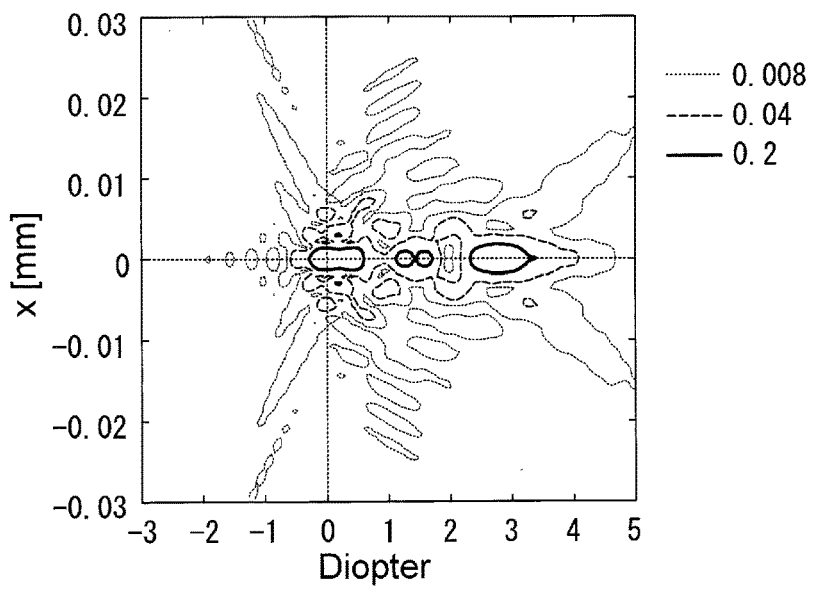
FIG. 6B is a view showing a simulation result of a point spread function formed at a predetermined position (for example, near the retina) in an eyeball to which the ophthalmic lens according to the first modification is attached in a case where the pupil diameter is 4 mm.
Figure 6C:
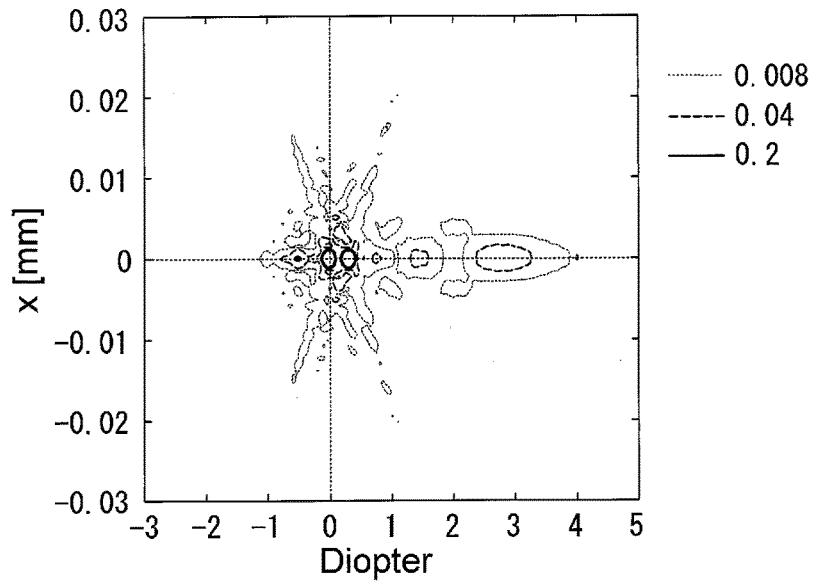
FIG. 6C is a view showing a simulation result of a point spread function formed at a predetermined position (for example, near the retina) in an eyeball to which the ophthalmic lens according to the first modification is attached in a case where the pupil diameter is 6 mm.

Further, FIG. 6A, FIG. 6B and FIG. 6C are graphs showing simulation results in each diopter of a point spread function (PSF) near the imaging point 34 in the eyeball 100 loaded with the intraocular lens 10 of the first modification. FIG. 6A shows a point spread function in a case where the pupil diameter is 3 mm, FIG. 6B shows a point spread function in a case where the pupil diameter is 4 mm, and FIG. 6C shows a point spread function in a case where the pupil diameter is 6 mm.

In each case, the simulation conditions are the same as those in the case of the simulation results shown in FIG. 3B and FIG. 4A to FIG. 4C.

It can be seen that the intraocular lens 10 of the first modification can increase values of the MTF and the point spread function in a defocus position from +1 to +4 diopters in each pupil diameter, that is, the depth of focus is increased. This means that while keeping the best imaging state for an object located at infinity (0 diopters), a certain good image for an object located at a distance between approximately 1 m to 25 cm from the eyeball can be obtained.

In the embodiment and the first modification described above, the effect of the increase in the depth of focus described above results from the fact that the first phase difference φ1 applied to the light ray passing through the first region Z1 with respect to the light ray passing through the third region Z3 is larger than the variation amplitude A3, A3a of the third phase difference φ3 applied to the light ray passing through the third region Z3. The first phase difference φ1 is not limited to 9.5 [rad] or 18 [rad] as described above. The effect of increase in the depth of focus described above is obtained so long as the first phase difference φ1 is 1.3 times or more as large as the variation amplitude A3, A3a of the third phase difference φ3.

Alternatively, the first phase difference φ1 applied to the light ray passing through the first region Z1 with respect to the light ray passing through the third region Z3 is not less than 3 [rad], and the variation amplitude A3, A3a of the third phase difference φ3 is not less than 0.1 [rad] and is smaller than the above-mentioned first phase difference φ1. This also increases the depth of focus described above.

Further, since the third phase difference φ3 that varies with the distance r from the optical axis AX with respect to the light ray passing through the third region Z3 is formed, the third region Z3 functions as a bifocal lens. This also contributes to the increase in the depth of focus described above.

Note that the first phase difference φ1 is not necessarily a constant value in the first region Z1, but may be a value that varies depending on the distance r from the optical axis AX.

In the embodiment and the first modification described above, the reference value (average value) of the third phase difference φ3 in the third region Z3 is 0 [rad]; however, this is not limited to 0 [rad], but may be any phase.

The first region Z1 may be, as one example, a region within a radius from the optical axis AX of less than 0.2 mm. The second region Z2 may be, as one example, a region located outside the first region Z1 with respect to the optical axis AX and within a radius from the optical axis AX of less than 1.2 mm. The third region Z3 may be, as one example, a region located outside the second region Z2 with respect to the optical axis AX and within a radius from the optical axis AX of less than 2.5 mm.

The pupil diameter of the human eyeball 100 is approximately 3 to 4 mm in a bright environment and approximately 6 mm in a dark environment. Therefore, by setting boundaries between the first region Z1, the second region Z2, and the third region Z3 to the above-described radii, an image of light rays passing through all of the first region Z1, the second region Z2, and the third region Z3 is formed on the retina 33 both in a bright environment and in a dark environment. Thus, the above-described effect of increasing the depth of focus can be obtained by the intraocular lens 10 both in a bright environment and in a dark environment.

Note that in the one embodiment and the first modification, an uneven shape is applied to the shape of the incident surface 11 or the exit surface 12 of the intraocular lens 10; however, a way of applying the first phase difference φ1, the second phase difference φ2, and the third phase difference φ3 is not necessarily limited to this way. For example, the above-described phase difference can also be applied by providing the first region Z1, the second region Z2, and the third region Z3 of the intraocular lens 10 with refractive index changing portions where the refractive index of the intraocular lens 10 varies with a higher-order function for the distance r from the optical axis AX. That is, for example, the intraocular lens 10 can be formed using a material having its refractive index changing concentrically around the optical axis AX (for example, silicone, acrylic resin, or the like).

Note that the above-described simulation may also be performed based on the shapes and the refractive indexes of the cornea 30, the anterior chamber 31, the intraocular lens 10, and the vitreous body 32 which constitute the eyeball 100. For example, a simulation may be performed employing values (curvature radius, refractive index, and the like) of the Navarro model disclosed in Table 36-16 of the above-mentioned document "Handbook of Optical Systems: Vol. 4 Survey of Optical Instruments".

Note that the shape and refractive index of the crystalline lens disclosed in Table 36-16 of the above-mentioned document are only typical examples. Thus, in a precise sense, the refractive power is generally different from the refractive power of the actual intraocular lens 10 which varies among individuals.

Therefore, in a simulation using the Navarro model, the simulation may be performed by appropriately changing the thickness of the intraocular lens 10 and the radii of curvature of the incident surface 11 and the reference surface 13 so that the imaging point 34 (focal point) positions on the retina 33 of the Navarro model.

Conversely, the above-described simulation approach can be used to determine whether or not a given intraocular lens is equivalent to the intraocular lens 10 of the embodiment or the modification described above. That is, the refractive index and the shape of the intraocular lens are numerically attached to the Navarro model, and the radii of curvature of the incident surface 11 and the reference surface 13 of the intraocular lens are appropriately changed to position the imaging point 34 (focal point) onto the retina 33 of the Navarro model. Under such conditions, the determination can be made based on whether or not a phase difference of each light ray passing through the first region Z1, the second region Z2, and the third region Z3 is the above-described phase difference.

The ophthalmic lens according to the present embodiment described above is not limited to the intraocular lens 10 (IOL) loaded in the eyeball 100 instead of the crystalline lens, but may be an implantable contact lens (IPL) loaded between the iris 36 and the crystalline lens. Further, the ophthalmic lens may be an intraocular lens for a so-called piggy bag which is additionally loaded for correction to the eyeball 100 to which the intraocular lens is attached. Alternatively, the ophthalmic lens may be a corneal inlay or a corneal onlay to be loaded into the cornea.

Alternatively, the ophthalmic lens may be a contact lens worn outside the cornea 30. In this case, the user can attach the contact lens having the configuration described in the present embodiment and an existing intraocular lens (for example, a single-focus type IOL) to an eye, for combined use. The ophthalmic lenses can also be used for various vision correction applications such as IOL that can be used for both pseudophakic and phakic applications.

Further, the ophthalmic lens may be a spectacle lens worn away from the eyeball.

Advantageous Effects of the One Embodiment and First Modification (1) As one aspect, the ophthalmic lens (intraocular lens 10) according to the one embodiment and the first modification described above is an ophthalmic lens attached in or near an eyeball 100, comprising a first region Z1 that is near an optical axis AX, a second region Z2 that is a portion farther from the optical axis AX than the first region Z1, and a third region Z3 that is a portion farther from the optical axis AX than the second region, wherein in a state where the intraocular lens 10 is attached to the eyeball 100, light rays passing through the first region Z1, the second region Z2, and the third region Z3 form an image on a retina 33. Then, the first region Z1 applies a first phase difference φ1 of 3 rad or more to the light ray passing through the first region Z1 with respect to the light ray passing through the third region Z3. The second region Z2 applies a second phase difference φ2 to the light ray passing through the second region Z2, the second phase difference φ2 continuously connecting phase differences of the light ray passing through the first region Z1 and the light ray passing through the third region Z3, and continuously changing in accordance with a distance r from the optical axis AX. The third region Z3 applies a third phase difference φ3 to the light ray passing through the third region Z3, the third phase difference φ3 varying in accordance with the distance r from the optical axis AX around a reference value, wherein a variation amplitude A3, A3a of the third phase difference φ3 is not less than 0.1 rad and less than the first phase difference φ1.

With this configuration, the depth of focus of the optical system of the eyeball 100 loaded with the intraocular lens 10 can be increased.

Moreover, since the phase of each imaging light ray changes continuously, the intraocular lens 10 can prevent generation of flare light which is generated due to the discontinuity of the phase, so that a clear view can be provided.

(2) As another aspect, the ophthalmic lens (intraocular lens 10) according to the one embodiment and the first modification described above is an ophthalmic lens attached in or near an eyeball 100, comprising a first region Z1 that is near an optical axis AX, a second region Z2 that is a portion farther from the optical axis AX than the first region Z1, and a third region Z3 that is a portion farther from the optical axis AX than the second region Z2, wherein in a state where the intraocular lens 10 is attached to the eyeball 100, light rays passing through the first region Z1, the second region Z2, and the third region Z3 form an image on a retina. Then, the third region Z3 applies a third phase difference φ3 to the light ray passing through the third region Z3, the third phase difference φ3 varying in accordance with the distance r from the optical axis AX around a reference value, with an amplitude being not less than 0.1 rad. The first region Z1 applies a first phase difference φ1 to the light ray passing through the first region Z1, the first phase difference φ1 being 1.3 times or more as large as the variation amplitude A3, A3a of the third phase difference φ3 applied to the light ray passing through the third region Z3. The second region Z2 applies a second phase difference φ2 to the light ray passing through the second region Z2, the second phase difference φ2 continuously connecting phase differences of the light ray passing through the first region Z1 and the light ray passing through the third region Z3, and continuously changing in accordance with a distance r from the optical axis AX.

With this configuration, the depth of focus of the optical system of the eyeball 100 loaded with the intraocular lens 10 can be increased.

Moreover, since the phase of each imaging light ray changes continuously, the generation of flare light generated due to the discontinuity of the phase can be prevented and a clear view can thus be provided.

(3) Further, the first region Z1 is a region within a radius from the optical axis AX of less than 0.2 mm, the second region Z2 is a region outside the first region Z1 and within a radius from the optical axis AX of less than 1.2 mm, and the third region Z3 is a region outside the second region Z2 and within a radius from the optical axis AX of less than 2.5 mm, so that an optimal imaging state can be maintained even when the pupil diameter changes due to ambient brightness.

(4) Furthermore, at least one of an incident surface 11 or an exit surface 12 of the first region Z1, the second region Z2, and the third region Z3 has a higher-order shape portion that changes in shape with a higher-order function for the distance r from the optical axis AX, wherein the first phase difference φ1, the second phase difference φ2, and the third phase difference φ3 are applied by the higher-order shape portion. This allows a material having a uniform refractive index to be used to configure the intraocular lens 10.

(5) Furthermore, the first region Z1, the second region Z2, and the third region Z3 have a refractive index variation portion that changes in refractive index with a higher-order function for the distance r from the optical axis AX, wherein the first phase difference φ1, the second phase difference φ2, and the third phase difference φ3 are applied by the refractive index variation portion. This allows the first phase difference φ1, the second phase difference φ2, and the third phase difference φ3 to be applied without forming an uneven shape in the incident surface 11 and the exit surface 12 of the interocular lens 10.

Second Modification

An intraocular lens 10 of a second modification is substantially the same as the intraocular lens 10 of the embodiment or the first modification described above, except that the above-described phase difference φ is represented by the following function φ(r) written by the following equation (2) in accordance with the distance r from the optical axis AX of each light ray.

$$\phi(r) = \sum_{j=1}^{J} C_j \mathrm{sinc}^g(D_j \zeta(r)) \quad (2)$$

Here, the function ζ(r) is written by the following equation (1).

$$\zeta(r) = \frac{n}{\lambda}\left(1 - \sqrt{1 - \left(\frac{r}{f}\right)^2}\right) \quad (1)$$

where f is a focal length of the intraocular lens 10, λ is a central wavelength of light used in the intraocular lens 10, and n is a refractive index of the intraocular lens. g is a first constant that is an arbitrary number larger than 0, and preferably a value of approximately 0.1 to 1.0.

sin c(x) is sin(πx)/(πx), and sin $c^g$(x) represents the g-th power of the absolute value of sin c(x) multiplied by a sign of sin c(x).

J is an arbitrary natural number, and each of the first factor Cj and the second factor Dj denotes J factors represented with a subscript j from 1 to J.

The first constant g, the first factor Cj, and the second factor Dj are set such that the phase difference φ(r) satisfies similar conditions as in the one embodiment and the first modification described above.

That is, the first constant g, the first factor Cj, and the second factor Dj are set such that the phase difference φ(r) varies with an amplitude of not less than 0.1 rad around the reference value in accordance with the distance r from the optical axis AX in the third region Z3, and a phase difference of 1.3 times or more as large as the above-described amplitude with respect to the above-described reference value is added in the first region Z1.

Alternatively, the first constant g, the first factor Cj, and the second factor Dj are set such that the phase difference φ(r) varies with an amplitude of not less than 0.1 rad around the reference value in accordance with the distance r from the optical axis AX and smaller than the first phase difference φ1, where the first phase difference φ1 between the first region Z1 and the third region Z3 is not less than 3 [rad].

Advantageous Effect of Second Modification

In the intraocular lens 10 of the second modification, similar effects as those of the one embodiment and the first modification described above can also be obtained. The shape of the incident surface 11 or the exit surface 12, or the refractive index distribution of the material constituting the intraocular lens 10 can be designed based on a sin c function, which is mathematically easy to handle, as an example of higher-order functions. Thus, the design and manufacture of the lens 10 are advantageously facilitated.

Third Modification

An intraocular lens 10 of a third modification is substantially the same as the intraocular lens 10 of the embodiment or the first modification described above, except that the above-described phase difference φ is represented by the following function φ(r) written by the following equation (4) in accordance with the distance r from the optical axis AX of each light ray.

$$\phi(r) = \sum_{j=1}^{J} C_j \operatorname{sinc}^g(D_j \zeta(r)) + \sum_{k=1}^{K} E_k \cos(S_k \zeta(r) + U_k) \quad (4)$$

Here, the functions ζ(r), g, sin c, sin $c^g(x)$, J, the first factor Cj, and the second factor Dj are the same as those in the second modification.

K is an arbitrary natural number, and each of the third factor Ek, the fourth factor Sk, and the fifth factor Uk denotes K factors represented with a subscript k from 1 to K.

The first constant g, the natural number J, the first factor Cj, the second factor Dj, the natural number K, the third factor Ek, the fourth factor Sk, and the fifth factor Uk are set such that the phase difference φ(r) satisfies similar conditions as in the one embodiment and the first modification described above, in the same manner as the second modification described above.

Advantageous Effect of Third Modification

The intraocular lens 10 of the third modification can also achieve similar effects as those in the intraocular lens 10 of the second modification described above. In the intraocular lens 10 of the third modification, a term written by the following equation (7) is added to the phase difference φ(r).

$$\sum_{k=1}^{K} E_k \cos(S_k \zeta(r) + U_k) \quad (7)$$

Thus, adjusting values in this term (values of the third factor Ek, the fourth factor Sk, and the fifth factor Uk) has an advantageous effect of easily setting the amplitude of the phase difference in accordance with the distance r from the optical axis AX in the third region Z3.

Fourth Modification

An intraocular lens 10 of a fourth modification is substantially the same as the intraocular lens 10 of the one embodiment or the first modification described above, except that the above-described phase difference φ is represented by the following function φ(r) written by the following equation (6) in accordance with the distance r from the optical axis AX of each light ray.

$$\phi(r) = C \exp[-(D\zeta(r))^2] + \sum_{k=1}^{K} E_k \cos(S_k \zeta(r) + U_k) \quad (6)$$

Here, the second constant C and the third constant D are arbitrary constants, and the function ζ(r), the third factor Ek, the fourth factor Sk, and the fifth factor Uk are the same as those in the third modification described above.

The second constant C, the third constant D, the natural number K, the third factor Ek, the fourth factor Sk, and the fifth factor Uk are set such that the phase difference φ(r) satisfies similar conditions as in the one embodiment and the first modification, in the same manner as the third modification described above.

Advantageous Effect of Fourth Modification

In the fourth modification, the function φ(r) has a first term that is a Gaussian function monotonically decreasing in accordance with the distance r from the optical axis, and a second term having a cos function that periodically varies with the distance r from the optical axis.

Therefore, the amplitude of the function φ(r) in accordance with the distance r from the optical axis AX in the third region Z3 can be mainly adjusted with the second term, and the phase difference φ1 between the light passing through the first region Z1 and the light passing through the third region Z3 can be mainly adjusted with the first term, in a generally independent manner. As an advantageous effect thereof, a user (in this case, a designer) can easily adjust (design) the function φ(r) for preferable conditions (for example, lens condition and the like).

Note that adjusting the first term means setting the second constant C and the third constant D, and adjusting the second term means setting the natural number K, the third factor Ek, the fourth factor Sk, and the fifth factor Uk.

Fifth Modification

In the intraocular lens 10 according to the one embodiment and the first to fourth modifications described above, the phase differences φ (the first phase difference φ1, the second phase difference φ2, and the third phase difference φ3) are rotationally symmetric with respect to the optical axis AX. However, the phase differences φ are not necessarily rotationally symmetric with respect to the optical axis AX.

An intraocular lens 10a according to a fifth modification has a phase difference that includes a phase difference two-fold symmetric with respect to the optical axis AX, in addition to the above-described phase difference φ of the intraocular lens 10 according to the one embodiment and the first to fourth modifications described above. Note that a function obtained by adding a two-fold symmetric function to a rotationally symmetric function is a two-fold symmetric function as a whole. Further, in the present embodiment including modifications described later, the phase difference of the ophthalmic lens is not limited to the two-fold symmetric phase difference, but may be a multi-fold symmetric phase difference such as a four-fold symmetric phase difference.

An example of a two-fold symmetric phase difference is, for example, a phase difference proportional to $y^2$ of a position (x, y) on the XY coordinates shown in FIG. 1A, which constitutes a so-called astigmatism.

In the graph of the phase difference φ shown in FIG. 3A or FIG. 5A, the two-fold symmetric phase difference can also be set by determining the phase difference φ, with the horizontal axis representing an index $v=\sqrt{(qx^2+y^2)}$, instead of the distance r ($=\sqrt{(x^2+y^2)}$) from the optical axis AX. Here, the factor q is a real number of approximately 0.5 to 2. With the factor q, an uneven shape formed on the intraocular lens 10a is enlarged by $(1/\sqrt{q})$ times in the X-axis direction (for example, one direction, a cross direction intersecting the Y-axis direction, an orthogonal direction orthogonal to the Y-axis direction), with respect to the Y-axis direction (for example, the other direction) in FIG. 1A.

Figure 10:
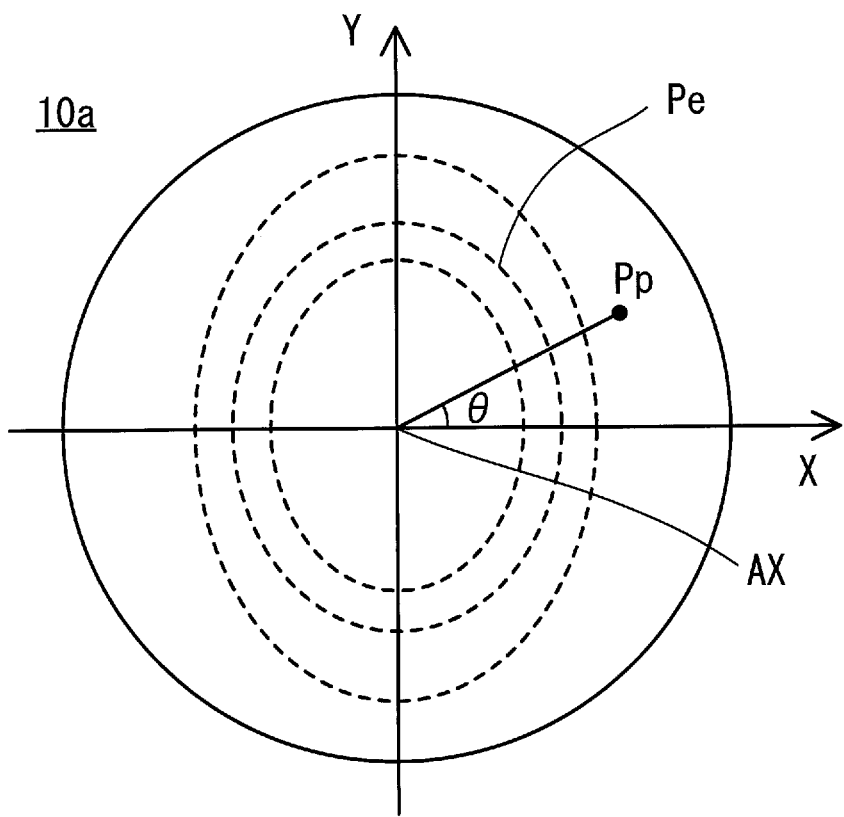
FIG. 10 is a view schematically showing an equiphase plane of the ophthalmic lenses according to a fifth modification and a sixth modification.

FIG. 10 is a view illustrating an example of an equiphase plane Pe of an imaging light ray that has passed through the intraocular lens 10a according to the fifth modification. FIG. 10 shows a top view of the intraocular lens 10a as in FIG. 1A and additionally shows the equiphase plane Pe connecting regions that have the same phase difference (for example, optical path length difference) formed by the intraocular lens 10a.

As described above, the uneven shape formed on the intraocular lens 10a is enlarged by ($1/\sqrt{q}$) times in the X-axis direction with respect to the Y-axis direction. Thus, for example, for q>1, the equiphase plane Pe is an ellipse having an axis length in the X-axis direction shorter than an axis length in the Y-axis direction.

Advantageous Effect of Fifth Modification (5) In the fifth modification, the phase difference φ applied by the intraocular lens 10 is set to be two-fold symmetric with respect to the optical axis AX, so that a focus position of an image in the X-axis direction and a focus position of an image in the Y-axis direction are offset in the optical axis direction. This has an effect of further increasing the substantial depth of focus.

The ophthalmic lens also has an effect of correcting astigmatism caused by the shape of the cornea 30 and the like.

Sixth Modification

An intraocular lens 10a of a sixth modification is a modification of the intraocular lens 10 according to the second modification and the third modification described above, and has a phase difference having a phase difference two-fold symmetric with respect to the optical axis AX as in the fifth modification described above. Therefore, a description will be made with reference to FIG. 10 described above.

In the intraocular lens 10a of the sixth modification, J first factors Cj in the intraocular lenses 10 of the second modification and the third modification are set as $Cj = Aj \cdot \cos^2\theta + Bj \cdot \sin^2\theta$. Here, as shown in FIG. 10, θ is an azimuth angle of a position Pp at which each light ray enters the intraocular lens 10a, from the optical axis AX with respect to the X axis. Each of the factor Aj and the factor Bj denotes J factors represented with a subscript j from 1 to J.

In the intraocular lens 10a of the sixth modification, a shape of an equiphase plane Pe of the imaging light ray that has passed through the intraocular lens 10a can also be made different (for example, two-fold symmetric) between in the X-axis direction and in the Y-axis direction, as in the fifth modification described above, by setting the first factor Cj as $Cj = Aj \cdot \cos^2\theta + Bj \cdot \sin^2\theta$ and setting the factor Aj and the factor Bj to different values.

Figure 11A:
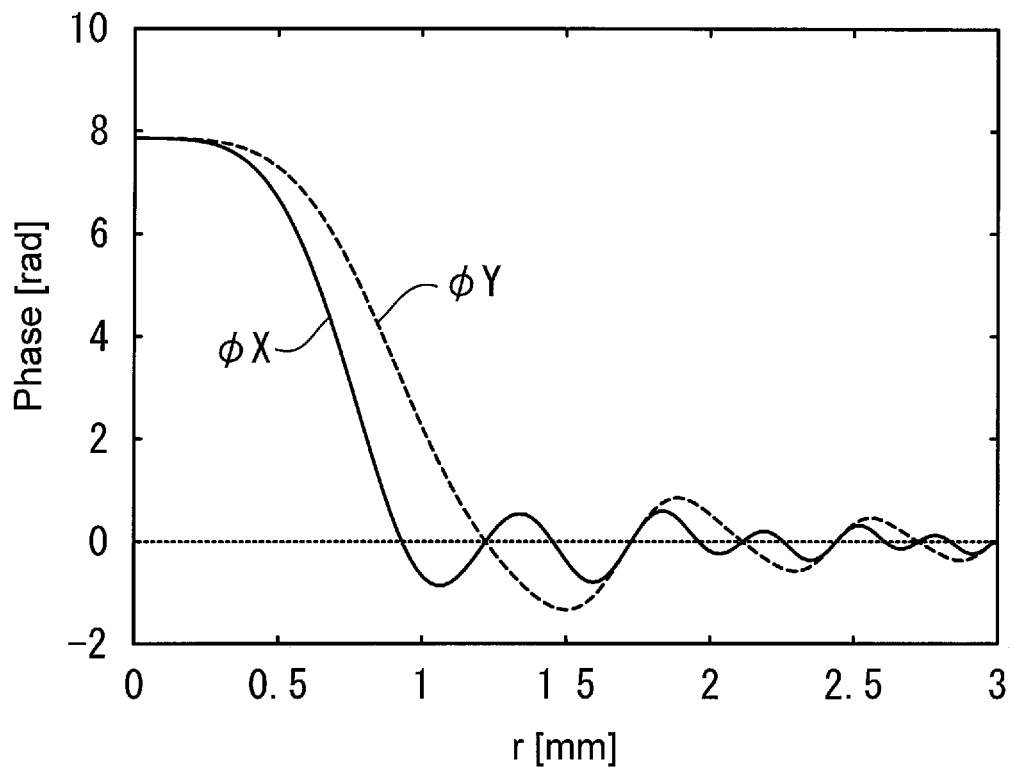
FIG. 11A is a view showing a phase change applied to an imaging light ray in an eyeball to which an ophthalmic lens according to the sixth modification is attached.

FIG. 11A is a graph showing an example of a phase difference of each imaging light rays reaching the imaging point 34 from an object, in the eyeball 100 loaded with the intraocular lens 10a according to the sixth modification. As described above, phase differences (for example, optical path length differences) applied by the intraocular lens 10a in the X-axis direction and the Y-axis direction are different. Thus, FIG. 11A shows the phase difference φX of the light ray passing on the X-axis of the intraocular lens 10a and the phase difference φY of the light ray passing on the Y-axis. Note that both the phase difference φX and the phase difference φY satisfy the conditions described in the embodiment or the first modification described above. Further, for example, as shown in FIG. 11A, the phase difference φX always continuously changes in accordance with the distance from the optical axis AX in each region and also has a variation of the amplitude that becomes gradually smaller as the distance from the optical axis AX increases in the X-axis direction, as in the above-described embodiment. Similarly, a variation of the amplitude of the phase difference φY becomes gradually smaller as the distance from the optical axis AX increases in the Y-axis direction. For example, the phase difference φ3 applied to the light ray at least in the third region in a predetermined direction of the intraocular lens 10a varies such that its amplitude gradually decreases based on the distance from the optical axis AX.

Figure 11B:
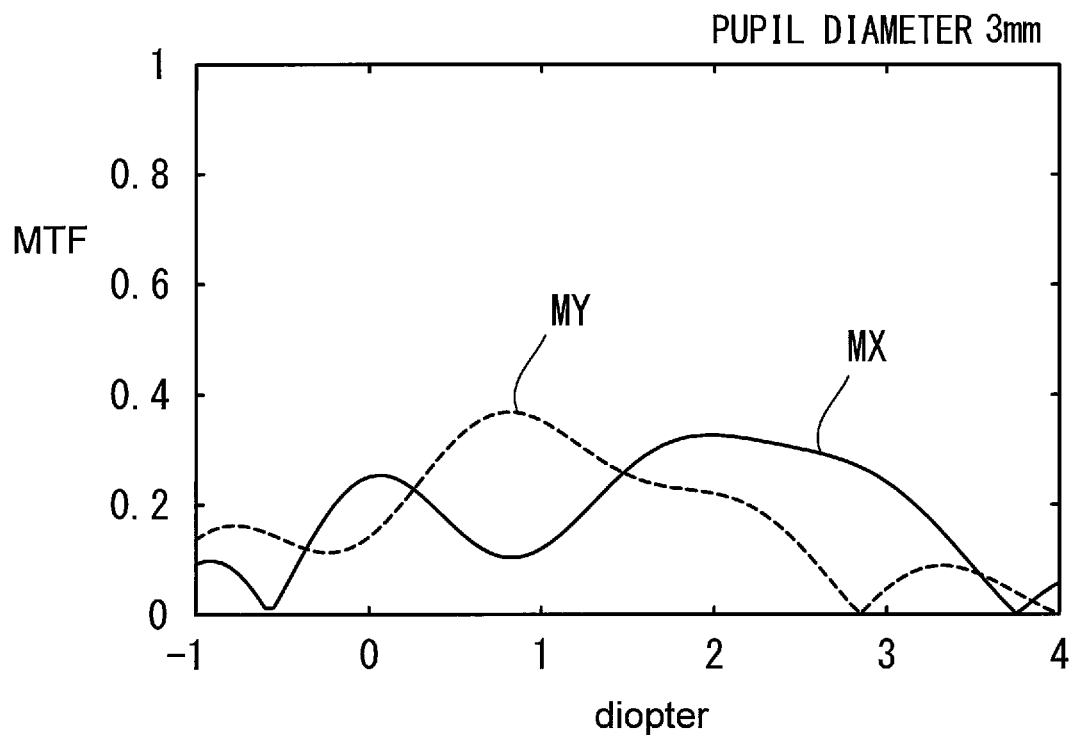
FIG. 11B is a view showing an MTF of an image formed on a retina in an eyeball to which the ophthalmic lens according to the sixth modification is attached.

FIG. 11B is a graph showing a simulation result in each diopter of an MTF of an image formed on the retina 33 near the imaging point 34 in the eyeball 100 loaded with the intraocular lens 10a of the sixth modification. The pupil diameter and the spatial frequency of the image on the retina 33 used for the simulation are the same as in the case of FIG. 3B.

In FIG. 11B, a solid line MX represents an MTF for an image having a periodicity in the X-axis direction in FIG. 10, and a broken line MY represents an MTF for an image having a periodicity in the Y-axis direction in FIG. 10.

The intraocular lens 10a of the sixth modification has a phase difference two-fold symmetric with respect to the optical axis AX (phase differences in the X-axis direction and the Y-axis direction are different), and thus has defocus characteristics of an image having a periodicity in the X direction and an image having a periodicity in the Y direction. As a result, for example, in a position where the MTF in the X-axis direction (MX) decreases, such as in a defocus state of +1 diopter in FIG. 11B, the MTF in the Y-axis direction (MY) compensates for the decrease. Thus, both (in this case, the MTFs in two directions, that is, the X-axis direction and the Y-axis direction) act in a complementary manner to improve the MTF. As a result, the MTF of the image can be increased in a wide range of defocus states, that is, the depth of focus can be increased.

Advantageous Effect of Sixth Modification

In the intraocular lens 10 of the sixth modification, the phase difference φ to be applied can also be a phase difference two-fold symmetric with respect to the optical axis AX, so that the MTF of an image can be increased in a wide range of defocus states, that is, the depth of focus can be increased.

Next, a method of manufacturing an ophthalmic lens according to the present embodiment described above will be described. The method of manufacturing an ophthalmic lens is a method of manufacturing an ophthalmic lens described in each embodiment, including a process step in which the ophthalmic lens is manufactured with a processing device (for example, a molding device, a cutting device, a polishing device, etc.) using design data indicating a lens shape of the ophthalmic lens. The method of manufacturing an ophthalmic lens includes a design step of designing the lens shape and generating the design data. Here, the design data can be generated by converting information (for example, design conditions) such as the phase difference φ into the lens shape.

Additionally, a lens set including a plurality of ophthalmic lenses of the present embodiment can be provided. In this case, the lens set includes a plurality of ophthalmic lenses according to the present embodiment having different depth of focus and different numbers of focal points (for example, multifocal points such as bifocal and trifocal points).

The present invention is not limited to the above description. Other aspects that can be considered within the scope of the technical idea of the present invention are also included in the scope of the present invention. The embodiment may combine all or some of the above-described aspects.

REFERENCE SIGNS LIST

10: intraocular lens, 100: eyeball, 11: entrance plane, 12: exit plane, 13: reference plane, AX: optical axis, r: distance from optical axis, 30: cornea, 31: anterior chamber, 32: vitreous body, 33: retina, 36: iris, Z1: first region, Z2: second region, Z3: third region, φ: phase difference, φ1: first phase difference, φ2: second phase difference, φ3: third phase difference

The invention claimed is:
1. An ophthalmic lens to be attached in or near an eyeball, comprising:
 a first region that is near an optical axis;
 a second region that is farther from the optical axis than the first region; and
 a third region that is farther from the optical axis than the second region, wherein:
 in a state where the ophthalmic lens is attached to the eyeball, light rays passing through the first region, the second region, and the third region form an image on a retina;
 the first region applies a first phase difference of 3 rad or more of a third phase difference to the light ray passing through the first region with respect to the light ray passing through the third region;
 the second region applies a second phase difference to the light ray passing through the second region, the second phase difference continuously connecting phase differences of the light ray passing through the first region and the light ray passing through the third region, and continuously changing in accordance with a distance from the optical axis; and
 the third region applies the third phase difference to the light ray passing through the third region, the third phase difference varying in accordance with the distance from the optical axis around a reference value, wherein a variation amplitude of the third phase difference is not less than 0.1 rad and less than the first phase difference.

2. An ophthalmic lens according to claim 1, wherein:
 the first phase difference being 1.3 times or more as large as the variation amplitude of the third phase difference applied to the light ray passing through the third region.

3. The ophthalmic lens according to claim 2, wherein:
 the first region is a region within a radius from the optical axis of less than 0.2 mm;
 the second region is a region outside the first region and within a radius from the optical axis of less than 1.2 mm; and
 the third region is a region outside the second region and within a radius from the optical axis of less than 2.5 mm.

4. The ophthalmic lens according to claim 3, wherein:
 at least one of an incident surface or an exit surface of the first region, the second region, and the third region has a higher-order shape portion that changes in shape with a higher-order function for the distance from the optical axis; and
 the first phase difference, the second phase difference, and the third phase difference are applied by the higher-order shape portion.

5. The ophthalmic lens according to claim 3, wherein:
 the first region, the second region, and the third region have a refractive index variation portion that changes in refractive index with a higher-order function for the distance from the optical axis; and
 the first phase difference, the second phase difference, and the third phase difference are applied by the refractive index variation portion.

6. The ophthalmic lens according to claim 4, wherein:
 the higher-order function includes a sin c function.

7. The ophthalmic lens according to claim 1, wherein:
 the first region, the second region, and the third region include a phase difference forming surface that applies the first phase difference, the second phase difference, and the third phase difference to the light rays.

8. The ophthalmic lens according to claim 7, wherein:
 the first phase difference, the second phase difference, and the third phase difference of a light ray passing on a first axis orthogonal to the optical axis are functions $\Delta\varphi(r)$ with respect to a distance r of the light ray from the optical axis; and
 given that f is a focal length of the ophthalmic lens, $\lambda$, is a center wavelength of light used in the ophthalmic lens, n is a refractive index of the ophthalmic lens, g is a first constant larger than 0, $\sin c(x)$ is $\sin(\pi x)/(\pi x)$, and $\sin c^g(x)$ is a product of an absolute value of $\sin c(x)$ raised to the g-th power and a sign of $\sin c(x)$, the function $\Delta\varphi(r)$ is represented by a function $\varphi(r)$ written by equation (2)

$$\phi(r) = \sum_{j=1}^{J} C_j \sin c^g(D_j \zeta(r)) \tag{2}$$

using an arbitrary natural number J, J first factors $C_j$, J second factors $D_j$, and a function $\zeta(r)$ written by equation (1)

$$\zeta(r) = \frac{n}{\lambda}\left(1 - \sqrt{1 - \left(\frac{r}{f}\right)^2}\right). \tag{1}$$

9. The ophthalmic lens according to claim 7, wherein:
 the first phase difference, the second phase difference, and the third phase difference of a light ray passing on a first axis orthogonal to the optical axis are functions $\Delta\varphi(r)$ with respect to a distance r of the light ray from the optical axis; and
 given that f is a focal length of the ophthalmic lens, $\lambda$, is a center wavelength of light used in the ophthalmic lens, n is a refractive index of the ophthalmic lens, g is a first constant larger than 0, $\sin c(x)$ is $\sin(\pi x)/(\pi x)$, and $\sin c^g(x)$ is a product of an absolute value of $\sin c(x)$ raised to the g-th power and a sign of $\sin c(x)$, the function $\Delta\varphi(r)$ is represented by a function $\varphi(r)$ written by equation (4)

$$\phi(r) = \sum_{j=1}^{J} C_j \sin c^g(D_j \zeta(r)) + \sum_{k=1}^{K} E_k \cos(S_k \zeta(r) + U_k) \tag{4}$$

using an arbitrary natural number J, J first factors $C_j$, J second factors $D_j$, an arbitrary natural number K, K third factors $E_k$, K fourth factors $S_k$, K fifth factors $U_k$, and a function $\zeta(r)$ written by equation (3)

$$\zeta(r) = \frac{n}{\lambda}\left(1 - \sqrt{1 - \left(\frac{r}{f}\right)^2}\right). \quad (3)$$

10. The ophthalmic lens according to claim 7, wherein:
the first phase difference, the second phase difference, and the third phase difference of a light ray passing on a first axis orthogonal to the optical axis are functions $\Delta\varphi(r)$ with respect to a distance r of the light ray from the optical axis; and given that f is a focal length of the ophthalmic lens, $\lambda$, is a center wavelength of light used in the ophthalmic lens, n is a refractive index of the ophthalmic lens, g is a first constant larger than 0, sin c(x) is $\sin(\pi x)/(\pi x)$, and sin $c^g(x)$ is a product of an absolute value of sin c(x) raised to the g-th power and a sign of sin c(x), the function $\Delta\varphi(r)$ is represented by a function $\varphi(r)$ written by equation (6)

$$\phi(r) = C\exp[-(D\zeta(r))^2] + \sum_{k=1}^{K} E_k \cos(S_k \zeta(r) + U_k) \quad (6)$$

using an arbitrary natural number K, K third factors Ek, K fourth factors Sk, K fifth factors Uk, and a function $\zeta(r)$ written by equation (5)

$$\zeta(r) = \frac{n}{\lambda}\left(1 - \sqrt{1 - \left(\frac{r}{f}\right)^2}\right). \quad (5)$$

11. The ophthalmic lens according to claim 7, wherein:
the first phase difference, the second phase difference, and the third phase difference are rotationally symmetric with respect to the optical axis.

12. The ophthalmic lens according to claim 7, wherein:
the first phase difference, the second phase difference, and the third phase difference are multi-fold symmetric with respect to the optical axis.

13. The ophthalmic lens according to claim 7, wherein:
J second factors Dj are represented by $$Cj = Aj \cdot \cos^2\theta + Bj \cdot \sin^2\theta$$

using J factors Aj and J factors Bj with respect to an azimuth $\theta$ of an incident position of the light ray onto the ophthalmic lens, from the optical axis with respect to the first axis.

14. The ophthalmic lens according to claim 7, wherein:
the third phase difference in the third region varies such that its amplitude decreases based on a distance from the optical axis.

15. The ophthalmic lens according to claim 1, wherein:
the ophthalmic lens is an intraocular lens that is loaded into an eyeball, instead of a crystalline lens.

16. The ophthalmic lens according to claim 1, wherein:
the ophthalmic lens is an implantable contact lens loaded between an iris and a crystalline lens.

17. The ophthalmic lens according to claim 1, wherein:
the ophthalmic lens is a corneal inlay or a corneal onlay to be loaded into the cornea.

18. The ophthalmic lens according to claim 1, wherein:
the ophthalmic lens is a contact lens that contacts a cornea.

19. The ophthalmic lens according to claim 1, wherein:
the variation amplitude of the third phase difference is 70% or less of the first phase difference.

20. The ophthalmic lens according to claim 19, wherein:
a period of the variation in the radius r direction of the third phase difference in the third region is 0.1 to 1.0 mm.

* * * * *